US011779274B2

(12) United States Patent
McCarthy et al.

(10) Patent No.: US 11,779,274 B2
(45) Date of Patent: *Oct. 10, 2023

(54) SYSTEMS AND METHODS FOR NEUROLOGIC REHABILITATION

(71) Applicant: MedRhythms, Inc., Portland, MA (US)

(72) Inventors: Owen McCarthy, Boston, MA (US); Brian Harris, Revere, MA (US); Alex Kalpaxis, Boston, MA (US)

(73) Assignee: MEDRHYTHMS, INC., Portland, ME (US)

(*) Notice: Subject to any disclaimer, the term of this patent is extended or adjusted under 35 U.S.C. 154(b) by 1063 days.

This patent is subject to a terminal disclaimer.

(21) Appl. No.: 16/569,388

(22) Filed: Sep. 12, 2019

(65) Prior Publication Data

US 2020/0138363 A1 May 7, 2020

Related U.S. Application Data

(63) Continuation of application No. 15/488,201, filed on Apr. 14, 2017, now Pat. No. 10,448,888.
(Continued)

(51) Int. Cl.
A61B 5/00 (2006.01)
A61B 5/11 (2006.01)
A61B 5/389 (2021.01)

(52) U.S. Cl.
CPC ............ *A61B 5/486* (2013.01); *A61B 5/112* (2013.01); *A61B 5/1124* (2013.01);
(Continued)

(58) Field of Classification Search
CPC ....... A61B 5/486; A61B 5/1124; A61B 5/112; A61B 5/4836; A61B 2562/0219;
(Continued)

(56) References Cited

U.S. PATENT DOCUMENTS 6,644,976 B2  11/2003  Kullok et al.
7,825,319 B2  11/2010  Turner
(Continued)

FOREIGN PATENT DOCUMENTS

CN  102138781  8/2011
CN  102139140  8/2011
(Continued)

OTHER PUBLICATIONS

International Search Report and Written Opinion for International Application No. PCT/US17/27742, dated Jul. 19, 2017; 8 pages.
(Continued)

*Primary Examiner* — Christian Jang
(74) *Attorney, Agent, or Firm* — Leason Ellis LLP

(57) ABSTRACT

A method and system for rehabilitation of a patient having a physical impairment by providing music therapy, the method being implemented on a computer system having one or more physical processors configured by machine-readable instructions which, when executed perform the method, includes receiving biomechanical data from the patient regarding repetitive movements of the patient and determining a baseline condition; determining a baseline beat tempo having a constant frequency based on the baseline condition; providing music to the patient, the music having beat signals at the baseline beat tempo; providing a cue to the patient to perform each repetitive movement in time with an associated beat signal; receiving time-stamped biomechanical data of the patient relating to the repetitive movements performed by the patient in time with the baseline beat signals; analyzing the biomechanical data to identify an onset time of one or more cycles of the repetitive movement; determining an entrainment parameter based on the onset time and the associated beat signal; modifying the baseline beat tempo based on the entrainment parameter;
(Continued)

and determining whether a goal beat tempo has been reached.

25 Claims, 31 Drawing Sheets

Related U.S. Application Data

(60) Provisional application No. 62/322,504, filed on Apr. 14, 2016.

(52) U.S. Cl.
CPC ............ *A61B 5/4836* (2013.01); *A61B 5/002* (2013.01); *A61B 5/0077* (2013.01); *A61B 5/1128* (2013.01); *A61B 5/389* (2021.01); *A61B 5/7264* (2013.01); *A61B 5/7275* (2013.01); *A61B 2562/0219* (2013.01)

(58) Field of Classification Search
CPC ... A61B 5/7275; A61B 5/1128; A61B 5/0488; A61B 5/0077; A61B 5/002; A61B 5/7264
See application file for complete search history.

(56) References Cited

U.S. PATENT DOCUMENTS

| | | | |
|---|---|---|---|
| 9,424,348 | B1 | 8/2016 | Riggs-Zeigen |
| 9,446,302 | B2 | 9/2016 | Gavish |
| 9,536,560 | B2 | 1/2017 | Jehan et al. |
| 10,448,888 | B2 * | 10/2019 | McCarthy ............ A61B 5/1124 |
| 2002/0107556 | A1 | 8/2002 | Mcloul et al. |
| 2007/0074617 | A1 | 4/2007 | Vergo |
| 2007/0113726 | A1 | 5/2007 | Oliver et al. |
| 2008/0097633 | A1 | 4/2008 | Jochelson et al. |
| 2008/0153671 | A1 | 6/2008 | Ogg et al. |
| 2010/0075806 | A1 * | 3/2010 | Montgomery ....... G09B 19/003 600/23 |
| 2010/0186578 | A1 | 7/2010 | Bowen |
| 2010/0240945 | A1 | 9/2010 | Bikko |
| 2012/0101411 | A1 | 4/2012 | Hausdorff et al. |
| 2013/0060166 | A1 | 3/2013 | Friedman et al. |
| 2013/0231942 | A1 | 9/2013 | Capik |
| 2015/0093729 | A1 | 4/2015 | Plans et al. |
| 2016/0055420 | A1 | 2/2016 | Karanam et al. |
| 2016/0067136 | A1 | 3/2016 | Raghavan et al. |
| 2016/0292881 | A1 | 10/2016 | Bose et al. |
| 2016/0370854 | A1 | 12/2016 | Steele |

FOREIGN PATENT DOCUMENTS

| | | |
|---|---|---|
| CN | 204468592 | 7/2015 |
| CN | 105771087 | 7/2016 |
| EP | 1819309 | 8/2007 |
| JP | 2003267899 | 9/2003 |
| JP | 2006102156 | 4/2006 |
| JP | 2007193907 | 8/2007 |
| JP | 2015202140 | 11/2015 |
| WO | 2004099942 | 11/2004 |
| WO | 2006038712 | 4/2006 |

OTHER PUBLICATIONS

European Search Report corresponding to European Patent Application No. 17783299.5; 7 pages.
Chinese Office Action corresponding to Chinese Patent Application No. 201780034526.3 dated Jan. 22, 2021; 16 pages.
Japanese Office Action corresponding to Japanese Patent Application No. 2019-505329 dated May 18, 2021; 17 pages.
Tomotaka ITO, (Constructing a measuring and evaluating system for a gait of human lower limbs), Proceedings of the 2009 JSME Conference on Robotics and Mechatronics, The Japan Society of Mechanical Engineers, May 24, 2009, 1P1-K05(1)-1P1-K05(4).

* cited by examiner

SYSTEMS AND METHODS FOR NEUROLOGIC REHABILITATION

CROSS-REFERENCE TO RELATED APPLICATIONS

This application is a continuation of U.S. Non-Provisional patent application Ser. No. 15/488,201, titled "SYSTEMS AND METHODS FOR NEUROLOGIC REHABILITATION," filed on Apr. 14, 2017, and issued as U.S. Pat. No. 10,448,888 on Oct. 22, 2019, which claims priority to U.S. Provisional Patent Application No. 62/322,504 filed on Apr. 14, 2016, entitled "Systems and Methods for Neurologic Rehabilitation," both of which are hereby incorporated by reference in their respective entireties herein.

TECHNICAL FIELD

The present disclosure relates generally to systems and methods for rehabilitation of a user having a physical impairment by providing music therapy.

BACKGROUND

Many controlled studies over the past decade have emphasized the clinical role of music in neurologic rehabilitation. For example, regimented music therapy is known to directly enable cognition, motor and language enhancement. The process of listening to music enhances brain activity in many forms, igniting a widespread bilateral network of brain regions related to attention, semantic processing, memory, cognition, motor function and emotional processing.

Clinical data supports music therapy enhancing memory, attention, executive function, and mood. PET scan research on the neural mechanisms behind music revealed that pleasant music can stimulate a widespread network between the cortical and subcortical region including the ventral striatum, nucleus accumbens, amygdala, insula, hippocampus, hypothalamus, ventral tegmental area, anterior cingulate, orbitofrontal cortex, and ventral medial prefrontal cortex. The ventral tegmental area produces dopamine and has a direct connection to the amygdala, hippocampus, anterior cingulate and prefrontal cortex. This mesocorticolimbic system, which can be activated by music, plays a critical role in mediating arousal, emotion, reward, memory attention, and executive function.

Neuroscience research has revealed how the fundamental organization processes for memory formation in music shares a mechanism with the non-musical memory processes. The basis of phrase groupings, hierarchical abstractions, and musical patterns have direct parallels in temporal chunking principles for non-musical memory processes. This implies that memory processes activated with music could translate and enhance non-musical processes.

Accordingly, there remains a need for improved devices, systems, and methods for protecting the use of user identity and for securely providing personal information.

SUMMARY

In one aspect of the disclosed subject matter, a method for rehabilitation of a patient having a physical impairment by providing music therapy is provided, the method being implemented on a computer system having one or more physical processors configured by machine-readable instructions which, when executed perform the method, includes receiving biomechanical data from the patient regarding repetitive movements of the patient and determining a baseline condition; determining a baseline beat tempo having a constant frequency based on the baseline condition; providing music to the patient, the music having beat signals at the baseline beat tempo; providing a cue to the patient to perform each repetitive movement in time with an associated beat signal; receiving time-stamped biomechanical data of the patient relating to the repetitive movements performed by the patient in time with the baseline beat signals; analyzing the biomechanical data to identify an onset time of one or more cycles of the repetitive movement; determining an entrainment parameter based on the onset time and the associated beat signal; modifying the baseline beat tempo based on the entrainment parameter; and determining whether a goal beat tempo has been reached.

In some embodiments, the method includes measuring the biomechanical data. The biomechanical data from the patient includes motion, acceleration and pressure associated with movement of the patient. In some embodiments, measuring biomechanical data from the patient includes capturing video associated with movement of the patient.

In some embodiments, measuring biomechanical data from the patient includes transmitting the data from sensors associated with the patient to the computer system.

In some embodiments, measuring biomechanical data from the patient includes extracting data corresponding to stride length, cadence, velocity, distance traveled, heel strike pressure or symmetry of a patient's gait.

In some embodiments, providing cues to the patient to perform repetitive movement comprising providing a visual or audible cue to the patient. A handheld device can be provided to display the visual or audible cues.

In some embodiments, determining an entrainment parameter includes determining the delay between the beat signal and the onset time of each repetitive movement.

In some embodiments if the delay between the beat signal and the onset time of the repetitive movement is substantially constant, the method includes increasing the baseline beat tempo towards the goal tempo.

In some embodiments providing music to the patient comprises selecting music having beat signals at the baseline beat tempo.

In some embodiments providing music to the patient comprises modifying existing music to have beat signals at the baseline beat tempo.

In some embodiments, the repetitive movement includes the patient's gait, the method further including analyzing the biomechanical data to classify the symmetry of the patient's gait; if the patient's gait is considered asymmetrical, providing a first modification to the music during movement of one of the patient's feet and a second modification to the music during movement of the other of the patient's feet. In some embodiments, the first and second modifications of the music are different, and include at least one of a change in chord, volume, and tempo.

In some embodiments, the method further includes analyzing the biomechanical data to classify a deficit in initiating gait, if the patient's initiation is problematic, providing haptic feedback to the patient to assist initiation.

In some embodiments, the method further includes providing a user interface allowing a user to provide a time-stamped notation regarding an aspect of the physical movement of the patient. The physical movement of the patient is analyzed based on the time-stamped notation and the biomechanical data.

In another aspect of the disclosed subject matter, a system for rehabilitation of a user having a physical impairment by providing music therapy is provided, the system includes a handheld device having a display for interacting with the patient; a music delivery device connected to the handheld device for supplying music to the patient, the music having beat signals at a baseline beat tempo; one or more sensors associated with the patient, the sensors measuring biomechanical parameters associated with repetitive physical movement of the patient and a transmitter for providing time-stamped biomechanical data from the patient and time-stamped beat signals to the handheld device; a computer system at least intermittently connected to the handheld device having one or more physical processors configured by machine-readable instructions to: receive biomechanical data of the patient regarding repetitive movements of the patient and determine a baseline condition; determine a baseline beat tempo having a constant frequency based on the baseline condition; provide music to the patient, the music having beat signals at the baseline beat tempo; provide instructions to the handheld device to provide a cue to the patient to perform a repetitive movement in time with an associated baseline beat signal; receive time-stamped biomechanical data of the patient and time-stamped beat signals; analyze the time-stamped biomechanical data to identify an onset time of one of more cycles of the repetitive movement; determine an entrainment parameter based on the onset time and the associated beat signal; provide instructions to the handheld device to modify the baseline beat tempo based on the entrainment parameter; and determine whether a goal beat tempo has been reached.

In some embodiments, the one or more sensors includes sensors for measuring motion, acceleration and pressure associated with movement of the patient.

In some embodiments, the one or more sensors includes an image capture device for capturing video associated with movement of the patient.

In some embodiments, a processor associated with the handheld or the computer is configured to extract data corresponding to one or more of stride length, cadence, velocity, distance traveled, heel strike pressure and symmetry of a patient's gait from one or more of the motion, acceleration, pressure data and video of the patient.

In some embodiments, a processor determines the delay between the beat signal and the onset time of the repetitive physical movement.

In some embodiments, the repetitive physical movement includes the patient's gait, wherein the computer system is configured by machine-readable instructions to analyze the biomechanical data to classify the symmetry of the patient's gait; and if the patient's gait is considered asymmetrical, provide instructions to the handheld device to provide a first modification to the music during movement of one of the patient's feet and the second modification to the music during movement of the other of the patient's feet. K save you In some embodiments the sensors include a haptic feedback mechanism; wherein the computer system is configured by machine-readable instructions to analyze the biomechanical data to classify a deficit in initiating gait; and if the patient's initiation is problematic, provide instructions to the handheld device to providing haptic feedback from the sensors to the patient to assist initiation.

BRIEF DESCRIPTION OF THE DRAWINGS

The foregoing and other objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein.

DETAILED DESCRIPTION

The present invention relates generally to systems, methods and apparatus for implementing a dynamic closed-loop rehabilitation platform system that monitors and directs human behavior and functional changes. Such changes are in language, movement, and cognition that are temporally triggered by musical rhythm, harmony, melody, and force cues.

Figure 1:
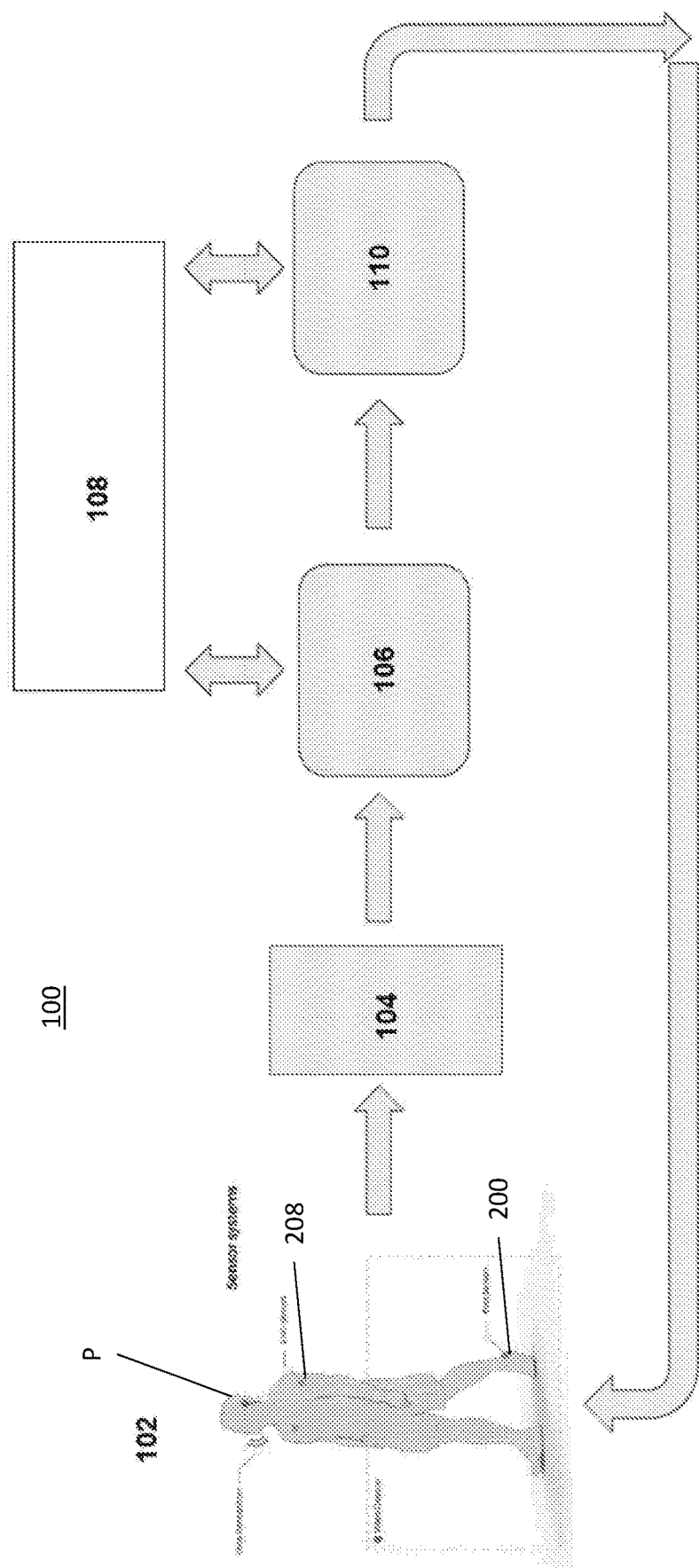
FIG. 1 is a diagram illustrating a system for therapy of a user by providing music therapy in accordance with exemplary embodiments of the disclosed subject matter.

In various embodiments of the invention, a dynamic closed-loop rehabilitation platform music therapy system 100 is provided illustrated in FIG. 1, which includes sensor components and systems 102, edge-processing components 104, collector components 106, analytics systems 108, and music therapy center 110. As will described in greater detail below, the sensor components, edge processing components, collector components machine learning processes and music therapy center may be provided on various hardware components. For example, in one embodiment, the sensor components and edge processing components may be located or worn by the patient. In such embodiments, the collector components and music therapy center may be provided on a handheld device. In such embodiments the analytics systems may be located on a remote server.

Sensor Systems

Throughout the description herein, the term "patient" is used to refer to the individual receiving musical therapy treatment. The term "therapist" is used to refer to the individual providing musical therapy treatment. In some embodiments, the patient is able to interact with this system described herein without the presence of the therapist to administer the treatment.

The sensor components 102 provide sensed biomechanical data about the patient. In some embodiments, the sensor components can include (1) wearable wireless real-time motion sensing devices or IMU (inertial measurement units), (2) wearable wireless real-time combination multiple zone foot plantar pressure/6-dimensional motion capture (IMU) devices, such as sensor 200, (3) wearable wireless real-time Electromyogram (EMG) devices, such as sensor 208 and (4) real-time wireless near infrared (NIR) video capture devices, such as imaging device 206 (See FIG. 4).

Figure 2:
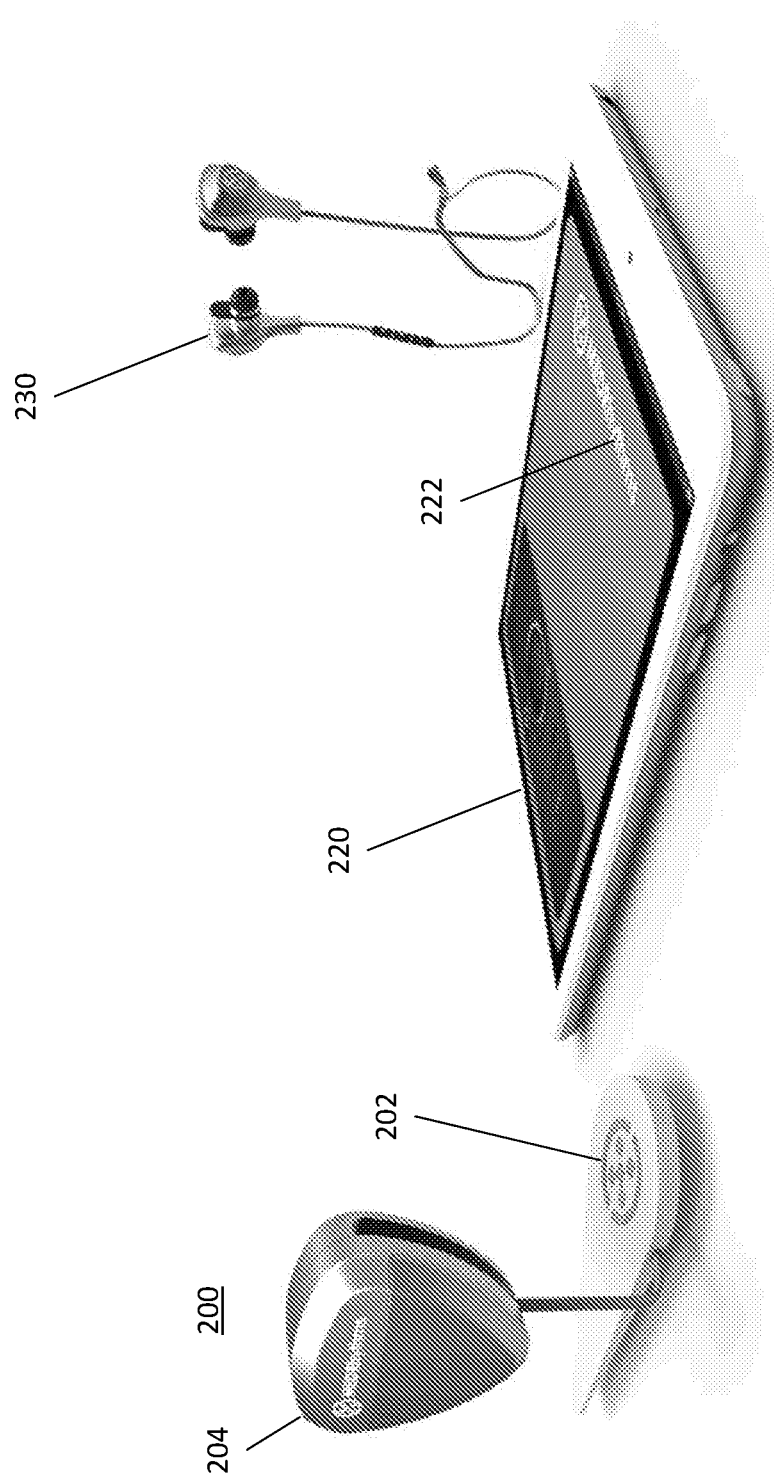
FIG. 2 is a diagram illustrating several components of a system for rehabilitation of a user by providing music therapy in accordance with exemplary embodiments of the disclosed subject matter.

As illustrated in FIG. 2, the systems and methods described herein are used in connection with treating walking disorders of the patient. Accordingly, the exemplary sensor 200 can be a combination multiple zone foot plantar pressure/6-degrees of freedom motion capture device. Sensor 200 records the patient's foot pressure and 6-degrees of freedom motion profile while the patient walks during a music therapy session. In some embodiments, the foot pressure/6-degrees of freedom motion capture device has variable recording duration intervals with a sampling rate of 100 Hz for a foot pressure profile that comprises 1 to 4 zones resulting in 100 to 400 pressure data points per foot per second.

The sensor 200 can include a foot pressure pad 202 having a heel pad (for measuring one zone of pressure, e.g., heel strike pressure) to a full insole pad (for measuring 4 zones of pressure). The pressure measurements are made by sensing the resistive changes in transducer material as a result of the compression due to the patient's weight transferred to the foot. These foot pressure maps are obtained for each sampling interval or at specific instants during a music therapy session.

The sensor 200 can include a 6-Dimensional motion capture device 204 that detects the changes in motion via a 6-degrees of freedom Micro-Electro-Mechanical Systems (MEMS) based sensor which determines linear acceleration in 3 dimensions, $A_x$, $A_y$, $A_z$ and rotational motion as pitch, yaw, and roll. Sampling at 100 Hz will produce 600 motion data points per second. These foot motion captures are obtained for each sampling interval or at specific instants during a music therapy session.

Figure 3:
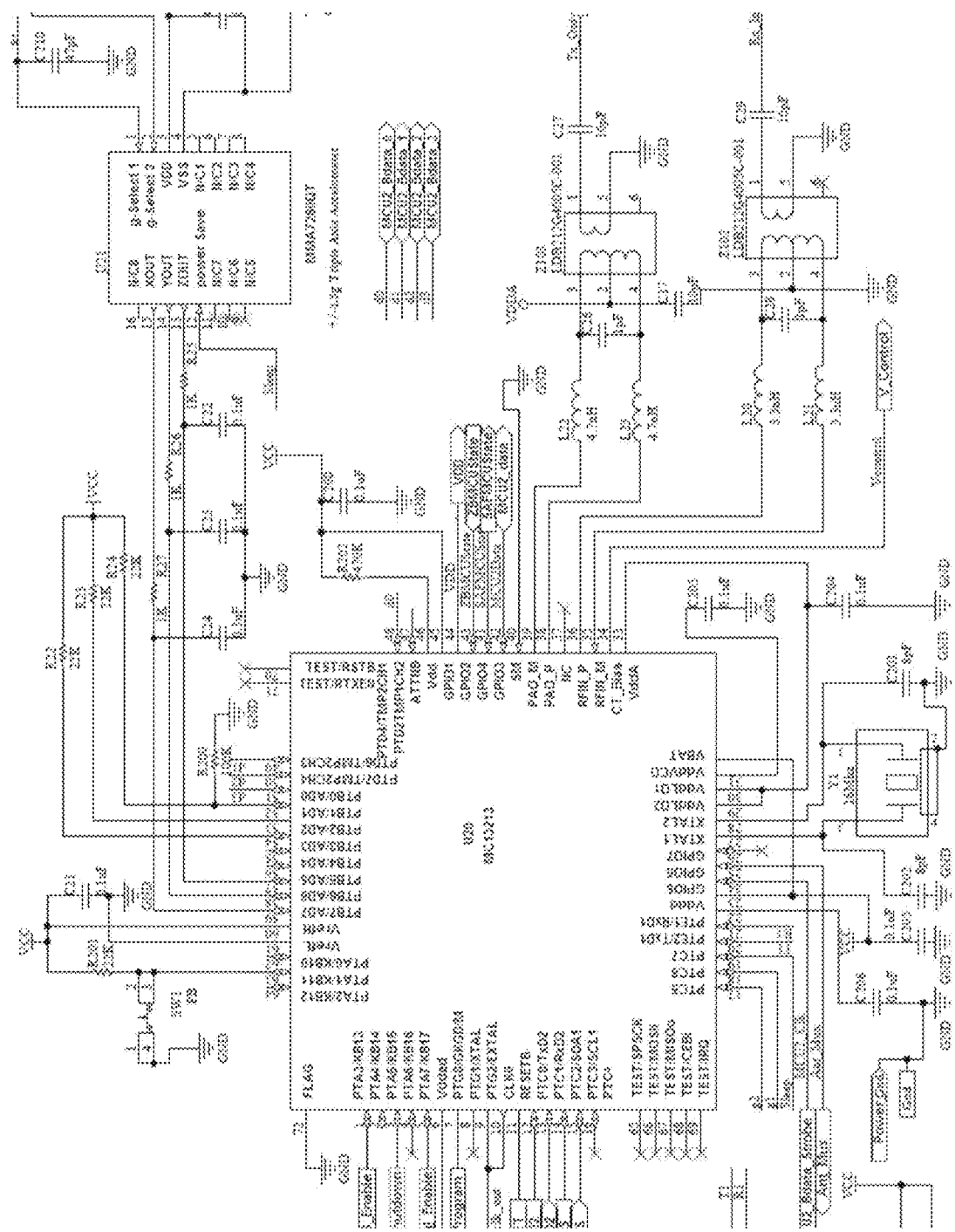
FIG. 3 is a schematic drawing of a sensor for measuring the biomechanical movements of a patient in accordance with exemplary embodiments of the disclosed subject matter.

The multiple zone pressure sensing with the 6-degrees of freedom motion capture device allows for map-able spatial and temporal gait dynamics tracking while walking. A schematic diagram of the sensor 200 is illustrated in FIG. 3.

Figure 4:
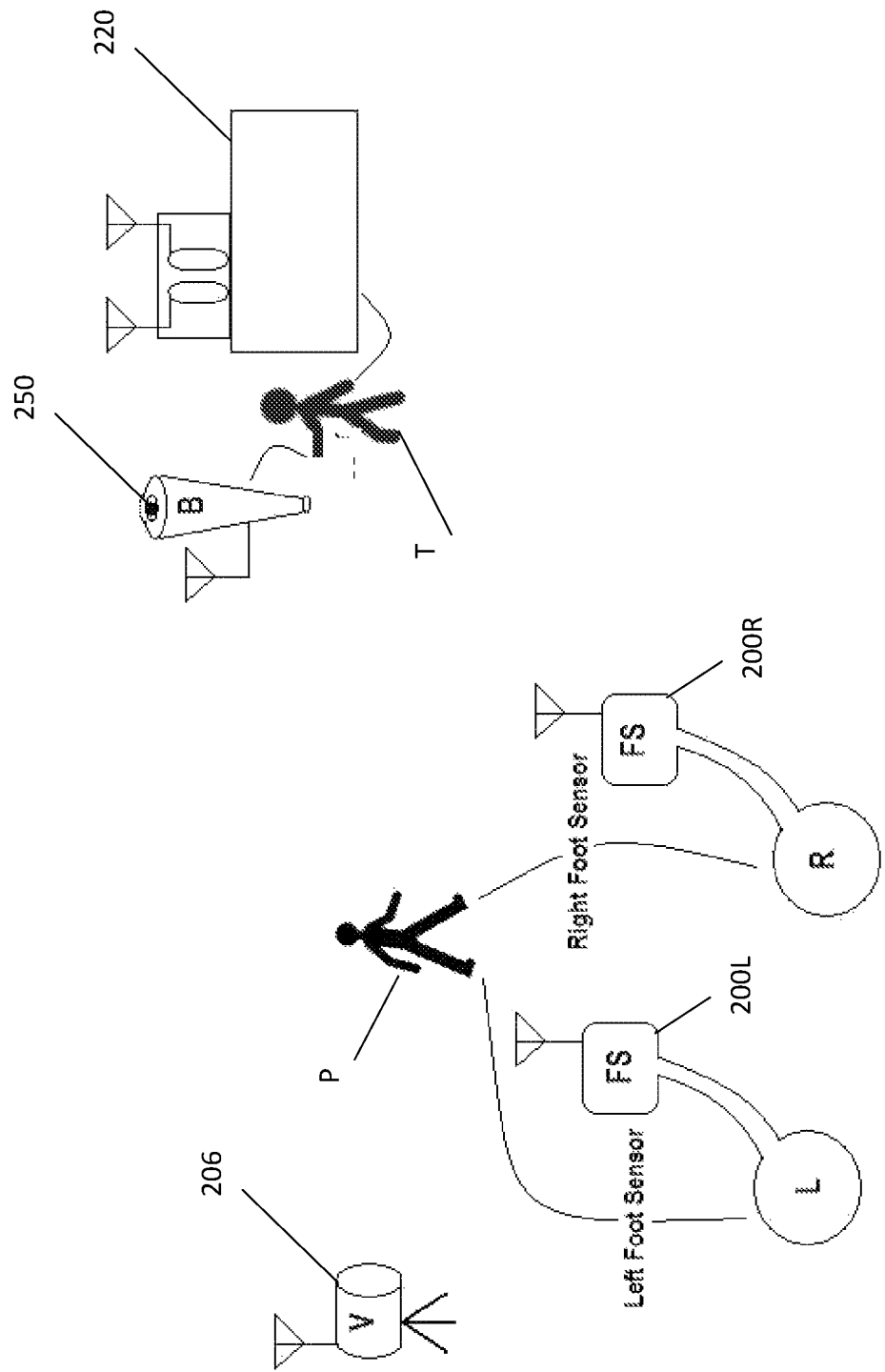
FIG. 4 is a diagram illustrating several components of the system in accordance with exemplary embodiments of the disclosed subject matter.

From a system perspective, as illustrated in FIG. 4, the patient P uses two foot sensors 200, one for each foot designated as Right 200R and Left 200L. In an exemplary embodiment, the right foot sensor 200R wirelessly communicates time-stamped internal measurement unit data and heel strike pressure data over a first channel, e.g., channel 5, in the IEEE 802.15.4 direct sequence spread spectrum (DSSS) RF band. The left foot sensor 200L wirelessly communicates time-stamped internal measurement unit data and heel strike pressure data over a second channel, e.g., channel 6, in the IEEE 802.15.4 direct sequence spread spectrum (DSSS) RF band. A tablet or laptop 220, optionally used by the therapist T, as described below, includes a wireless USB hub containing two IEEE 802.15.4 DSSS RF transceivers tuned to the first and second channels, e.g., channel 5 and 6, in order to capture the right/left foot sensor RF data. A handheld wireless trigger 250 is used to start and stop video and/or to make notations and index the time stream as discussed in greater detail below.

A video analytics domain can be used to extract patient semantic and event information about therapy sessions. Patient actions and interactions are components in the therapy that affect the therapy context and regiment. In some embodiments, one or more image capture devices 206, such as video cameras, (see FIG. 4) are used with a time-synched video feed. Any appropriate video may be incorporated into the system to capture patient movement; however, Near Infrared (NIR) video capture is useful to preserve the patient's privacy and to reduce the video data to be processed. The NIR video capture device captures NIR video images of a patient's body such as the position of the patient's torso and limbs. Further, it captures the patient's real-time dynamic gait characteristics as a function of a music therapy session. In some embodiments, the video is captured with a stationary camera, in which the background is subtracted to segment out foreground pixels.

As illustrated in FIG. 4, the one or more video cameras 206 are triggered by the tablet or laptop application when therapy session starts. The video cameras 206 can be stopped or started by a hand held wireless trigger unit 250 by the therapist. This allows for labeled time-stamped index to be created in the captured biomechanical sensor data and video data streams.

In some embodiments, wearable wireless real-time Electromyogram (EMG) devices 208 can be worn by the patient. EMG sensors provide the entire bi-ped profile for major muscle firing for locomotion. Such sensors provide data regarding the exact time when the muscle are fired.

Edge Processing

In some embodiments, the edge process is performed at the sensors 200, where sensor data is captured from the IMU and pressure sensors. This sensor data is filtered, grouped into various array sizes for further processing into frames reflecting extracted attributes and features, and where these frames are sent, e.g., wirelessly, to the collector 106 on a tablet or laptop. It is understood that the raw biomechanical sensor data obtained from the sensor 200 can alternatively be transferred to a remote processor for the collect for the edge processing functions to take place.

The wearable sensors 200, 208 and the video capture devices 206, generates sensor data streams that are processed holistically to facilitate biomechanical feature extraction and classification. Sensor fusion, combining the outputs from multiple sensors capturing a common event, better captures a result than any single constituent sensor inputs.

Capturing patient activities in the music therapy context formalizes the interactions as applied to the music therapy and in developing patient specific and generalized formal indicators of the music therapy performance and efficacy. Extracting video features and then analyzing allows for the capture of semantic, high-level information about patient behaviors.

In processing video, a learned background subtraction technique is used to create a background model which incorporates any variation in lighting conditions and occlusions in the physical area where music therapy occurs. The result of the background subtraction is a binary foreground map with an array of foreground blobs which are two dimensional contours. Thus, the video is sliced into individual image frames for future image processing and sensor fusion. Video information is provided with additional meta data by merging in the edge-processed sensor data from the IMU, foot pressure pad(s), and EMG sensors. The sensor data can be time synched with the other data using the RF trigger. Data can be sent directly to the collector, stored on the memory of the internal board, or analyzed on the edge running the OpenCV library.

The edge processor 104 can be a microprocessor, such as a 32-bit microprocessor incorporated into the foot pressure/6-degrees of freedom motion capture device that enables fast multiple zone scanning at a rate of 100 to 400 complete foot pressure/6-degrees of freedom motion profiles per second.

The foot pressure/6-degrees of freedom motion capture device collects foot pressure/6-degrees of freedom motion profile data for real-time gait analysis resulting in feature extraction and classification. In some embodiments, the foot pressure/6-degrees of freedom motion capture device initializes an micro controller unit (MCU), continuous operator process (COP), general purpose input output (GPIO), serial peripheral interface (SPI), interrupt request (IRQ), and sets a desired RF transceiver clock frequency by calling routines including micro controller unit initialize (MCUInit), general purpose input output initialize (GPIOInit), serial peripheral interface initialize (SPIInit), interrupt request acknowledge-initialize (IRQInit), interrupt request acknowledge (IRQACK), Serial Peripheral Interface Driver Read (SPIDrvRead), and IRQPinEnable. MCUInit is the master initialization routine which turns off the MCU watchdog and sets the timer module to use bus clock (BUSCLK) as a reference with a pre-scaling of 32.

The state variable gu8RTxMode is set to SYSTEM_RESET_MODE and the routines GPIOInit, SPIInit and IRQInit are called. The state variable gu8RTxMode is set to RF_TRANSCEIVER_RESET_MODE and the IRQFLAG is checked to see if IRQ is asserted. The RF transceiver interrupts are first cleared using SPIDrvRead, then the RF transceiver is checked for ATTN IRQ interrupts. Lastly, for MCUInit, calls are made to PLMEPhyReset to reset the physical MAC layer, IRQACK (to ACK the pending IRQ interrupt) and IRQPinEnable which is to pin, Enable, IE, and IRQ CLR, on signal's negative edge.

The foot pressure/6-degrees of freedom motion sensor 200 will wait for a response from the foot pressure/6-degrees of freedom motion collecting node, e.g., 250 milliseconds, to determine whether a default full foot pressure scan will be done or a mapped foot pressure scan will be initiated. In the case of a mapped foot pressure scan, the foot pressure/6-degrees of freedom motion collecting node will send the appropriate electrode the foot pressure scan mapping configuration data.

One aspect of the analytics pipeline is the feature set engineering process which will define those captured sensor values and their resulting sensor-fused values that are used to create feature vectors to define the input data structures for the analytics. Representative values are $Ax(i)$, $Ay(i)$, $Az(i)$, and $Ph(i)$, where i is the ith sample, where $Ax(i)$ is the acceleration in the x-direction which is Lateral in relation to the foot sensor; $Ay(i)$ is the acceleration in the y-direction which is Front in relation to the foot sensor; $Az(i)$ is the acceleration in the z-direction which is Up in relation to the foot sensor; and $Ph(i)$ is the heel strike pressure. The Sensor values are presented in Table 1:

TABLE 1

Avg (Ax) = Sum [Ax(i) over i = 0 to i = N]/N
Avg (Ax) = Sum [Ax(i) over i = 0 to i = N]/N
Avg (Ay) = Sum [Ay(i) over i = 0 to i = N]/N
Avg (Az) = Sum [Az(i) over i = 0 to i = N]/N
Max (Ax) in the range of Ax(i) from i = 0 to i = N
Max (Ay) in the range of Ay(i) from i = 0 to i = N
Max (Az) in the range of Az(i) from i = 0 to i = N
Min (Ax) in the range of Ax(i) from i = 0 to i = N
Min (Ay) in the range of Ay(i) from i = 0 to i = N
Min (Az) in the range of Az(i) from i = 0 to i = N
Avg (Ph) = Sum [Ph(i) over i = 0 to i = N]/N
Max (Ph) in the range of Ph(i) from i = 0 to i = N
where N = window size In some embodiments, the sensor-fused technique uses the heel strike pressure value $Ph(i)$ to "gate" the analysis of the following exemplary feature values to derive a window of data as will be described below. For example, the "onset" (start) can be determined based on heel pressure exceeding a threshold indicating heel strike, and the "stop" based on heel pressure falling below a threshold indicating heel off, presented in Table 2, below. It is understood, that heel strike pressure is one example of a parameter that can be used to for the "gate" analysis. In some embodiments, "gating" is determined by use of IMU sensor data, video data, and/or EMG data.

TABLE 2

Power Factor $PF(i) = \text{Sqrt}(Ax(i)^{}2 + Ay(i)^{}2 + Az(i)^{**}2)$
Windowed Total Motion Intensity = $[Avg(Ax) + Avg(Ay) + Avg(Az)]/3$
Windowed Lateral Tremor Intensity = $\text{Sum}[(Ax(i) - Ax(i+1))^{**}2]$ from $i = 0$ to $i = N$
Windowed Total Tremor Intensity =
Sum $[(Ax(i) - Ax(i+1))^{**}2]$ +
Sum $[(Ay(i) - Ay(i+1))^{**}2]$ +
Sum $[(Az(i) - Az(i+1))^{**}2]$ from $i = 0$ to $i = N$
Windowed Differential $Ax = \text{Max}(Ax) - \text{Min}(Ax)$
Windowed Differential $Ay = \text{Max}(Ay) - \text{Min}(Ay)$
Windowed Differential $Az = \text{Max}(Az) - \text{Min}(Az)$
where N = window size Higher level feature values are calculated from the fused sensor values, such as exemplary values presented in Table 3:

TABLE 3

Step Count (Total number)
Step Length Right (centimeters - cm)
Step Length Left (cm)
Step Time Right (milliseconds - msec)
Step Time Left (msec)
Asymmetry Factor Right/Left Step Time (Step Time Right - Step Time Left)
Step Width (cm)
Cadence (strides per minute)
Stride Length (cm)
Stride Velocity (cm/sec)
Stride Time Right (msec)
Stride Time Left (msec)
Asymmetry Factor Right/Left Stride Time (Stride Time Right - Stride Time Left)
Stride Tremor (Windowed Lateral Tremor Intensity)
Stride Fluidity (Windowed Total Tremor Intensity)
Stride Tremor Accumulated (Windowed Lateral Tremor Intensity)
Stride Fluidity Accumulated (Windowed Total Tremor Intensity)
Swing Time Right Foot (msec)
Swing Time Left Foot (msec)
Stance Phase Right Foot (msec)
Stance Phase Left Foot (msec)
Asymmetry Factor Stance Phase Right/Left Stance Phase (Stance Phase Right-Stance Phase Left)
Double Support Stance Time (msec)
Vertical Displacement [Mid-Stance] Max (cm)
Vertical Displacement [Double Support] Min (cm)
Heel Strike Time Right Foot (msec)
Heel Strike Time Left Foot (msec)
Heel Strike Pressure Right Foot (shift N - Newton)
Heel Strike Pressure Left Foot (N)
Asymmetry Factor Right/Left Heel Strike Pressure (Heel Strike Pressure Right Foot - Heel Strike Pressure Left Foot)
Distance Travelled Accumulated (meters - m)
Average Velocity (m/min)
Variability of each of the factors The system described herein provides the capability to "gate" or provide a "window" with respect to the patient biomechanical data. Gating of the biomechanical data is useful for repetitive patient movements, such as the repetitive strides while a patient is walking. Sensor data, from one or more sources, such as pressure sensors, IMU sensors, video data, and EMG data, is used to identify cycles of movement that repeat over time. For example, when a patient walks, foot pressure increases and decreases repetitively, as the patient's foot contacts the ground and then is lifted off the ground. Likewise, the velocity of the foot increase as the foot moves forward and decreases to zero while the foot is planted on the ground. As a further example, the Y-position or height of the patient's foot cycles between a low position (on the ground) and a high position (approximately in mid stride). The "gating" technique identifies repeating cycles or "windows" within such data. In the case of a patient walking, the cycle is repeated with each step. Although there may be variations between cycles, e.g., between steps, certain patterns repeat with each cycle. Selecting an onset time (start time) of each cycle involves locating an identifiable point (maximum or minimum) of a biomechanical parameter. The selection of the parameter for the onset time is selected based upon the available data. Thus, in some embodiments, the moment when the heel-strike pressure exceeds a threshold may be used to demarcate the onset time of each cycle. (See, e.g., FIG. 5. Pressure 316a and 316b includes a cyclic characteristic. "Onset" may be determined at the moment the pressure exceeds a threshold.) Similarly, the onset time may be demarcated when foot velocity falls to zero.

In some embodiments, raw frames data is pre-processed, taking the instant data and "gating" it, e.g., identifying a window, and then analyzing data within that window to identify outliers and to perform analysis on the data, e.g., exponential analysis, averaging data among multiple windows. Fusion of sensor data, by including both IMU data and heel-strike pressure data, allows for more precise identification of onset times for a single stride or other repeated units of motion than using data from a single sensor. Sensor data captured within a single stride is considered a "window," and information extracted from this analysis includes, e.g., stride length, step count, cadence, time when step occurs, distance traveled, stance phase/swing phase, double support time, velocity, symmetry analysis (e.g., between left and right leg), outward swing, shuffling, power vector, lateral acceleration, step width, variability of each of these dimensions, additional parameters derived from the above-described information, etc. Feature extraction can be processed on microprocessor chip, e.g., a 32-bit chip. Capture of wireless synchronous-gated biomechanical sensor data and video data capture capability allows for time-series template creation.

The data can be indexed by the patient or the therapist during a music therapy session. The "gating" functionality described above is useful to tie exception conditions to particular strides or steps. For example, the therapist may observe a particular exception condition or behavior (such as an anomaly or incident) in the patient's movement. The indexing function allows the therapist to initiate, such as, capture to "record," an exception condition or behavior via a user interface on the handheld tablet or laptop, such as the wireless trigger unit 250 illustrated in FIG. 4, or voice control. A notation can be created that includes a timestamp and a comment, such as the occurrence of a "stumble" by the patient while walking. Such indexing facilitates time-series template creation. These time-series templates will be studied for review of therapy session events and for the development of times-series templates for training machine learning algorithms such as non-linear multi-layered perceptrons (NLMLP), convolutional neural networks (CNNs), and recurrent neural networks (RNNs) with long short term memory (LSTM).

In one embodiment, a communication protocol is provided to transfer sensor data from edge processing 104 (e.g. at the sensors 200) to the collector 106. See Table 4 below. In some embodiments, if the connection is idle for more than 100 ms, the RF has timed out.

TABLE 4

| [0x10] | Start of frame |
|---|---|
| [0x49] | FootClipSensor ID = 'I' |
| [0x52] or [0x4C] | Which FootClipSensor = 'R' or 'L' |
| [0x00~0xFF] | Zone 1 |
| [0x00~0xFF] | Zone 2 |
| [0x00~0xFF] | Zone 3 |
| [0x00~0xFF] | Zone 4 |
| [Az] | Az |
| [Ay] | Ay |
| [Ax] | Ax |
| [HighByteSeqNum] | High Byte Sequence |
| [LowByteSeqNum] | Low Byte Sequence |

In one embodiment, the foot pressure sensor zone scanning is performed by the FootScan routine where the FootDataBufferindex is initialized and the foot pressure sensor zone is activated by enabling MCU direction mode for output [PTCDD_PTCDDN=Output] and bringing the associated port line low [PTCD_PTCD6=0]. As the foot pressure sensor zone is activated based on the foot pressure sensor zone scanning map, the foot pressure sensor zones attached to the MCU analog signal ports will be sampled and then the current voltage reading converts them into digital form (which is the-time zone foot pressure).

Several variables such as FootDataBufferindex and IMUBufferIndex are used to prepare the IEEE 802.15.4 RF packets gsTxPacket.gau8TxDataBuffer[ ] which are for sending the data to be used in FootDataBuffer[ ] and IMUBuffer[ ]. The RF packets are sent using the RFSendRequest (& gsTxPacket) routine. This routine checks to see if gu8RTxMode is set at IDLE_MODE and uses gsTxPacket as a pointer to call the RAMDrvWriteTx routine which then calls SPIDrvRead to read the RF transceiver's TX packet length register contents. Using these contents, mask length settings update and then add 2 for CRC and 2 for code bytes.

SPISendChar is called to send a 0x7E byte, which is the 2nd code byte and then the SPIWaitTransferDone is called again to verify the send is done. With these code bytes sent, then the rest of the packet is sent using a for loop, where psTxPkt→u8DataLength+1 are the number of iterations to a series of sequential to SPISendChar, SPIWaitTransferDone, SPIClearRecieveDataReg. When complete, the RF transceiver is loaded with the packet to send. The ANTENNA_SWITCH is set to transmit, the LNA_ON mode enabled, and finally a RTXENAssert call made to actually send the packet.

Collector

The primary function of the collector 106 is to capture data from the edge processing 104, transfer data to and receive processed data from the analytics system 108, and transfer data to the music therapy center 110, described below. In some embodiments, the collector 106 provides control functionality, e.g., a user interface to login, configure the system, and interact with users, and includes a display unit to visualize/display data. The collector 106 may include lightweight analytics or machine learned algorithms for classification (e.g., lateral tremor, asymmetry, instability, etc).

The collector 106 receives body, motion, and localization data from the edge processor 104. Data received at collector 106 can be raw or processed at the edge 104 prior to transfer to the collector. For example, the collector 106 receives fused sensor data, subject to "windowing" and feature extraction. The transferred data can include two levels of data: (1) RF Packets sent from the Right/Left foot sensors as described in Table 1, (2) RF Packets from the Right/Left foot sensors which contains higher level attributes and features as described in Tables 2 and 3. The collector 106 locally stores the data. In some embodiments, the collector 106 classifies movement from the received data, e.g., comparing it to models stored locally (pre-downloaded from the analytics system) or sent to analytics system for classification. The collector may include a display unit to visualize/display the data.

In some embodiments the collector 106 operates on a local computer that includes a memory, a processor and a display. Exemplary devices on which the collector is installed can include AR devices, VR devices, tablets, mobile devices, laptop computers, desktop computers, and the like. FIG. 2 illustrates a handheld device 220 having a display 222, and which performs the collector functions. In some embodiments, the connection parameters for transferring data between the patient sensor and the collector are made include the use of Device Manager in Windows (e.g., Baud rate: 38400, data bits: 8; parity: none, stop bits: 1). In some embodiments, the collector 106 includes a processor that is held or worn by the music therapy patient. In some embodiments, the collector 106 includes a processor that is remote from the music therapy patient and carried by a therapist, and connected wirelessly or via a wired connection to the music therapy patient.

In one embodiment, a foot pressure/6-degrees of freedom motion collecting node captures RF transmitted data packets containing real-time foot pressure/6-degrees of freedom motion profile data from the foot pressure/6-degrees of freedom motion capture device. This is started by the foot pressure/6-degrees of freedom motion collecting node which creates a RF packet receive queue that is driven by a call back function on RF transceiver packet receive interrupts.

When an RF packet is received from a foot pressure/6-degrees of freedom motion capture device 200, a check is first made to determine if this from a new foot pressure/6-degrees of freedom motion capture device or an existing one. If this is from an existing foot pressure/6-degrees of freedom motion capture device, RF packet sequence numbers are checked to determine continuous synchronization before further analyzing the packet. If this is a foot pressure capturing/6-degrees of freedom motion device, a foot pressure/6-degrees of freedom motion capture device context state block is created and initialized. The context state block includes information, e.g., the foot pressure profile, [what additional information?]

Above this RF packet session level process for node to node communication, is the analysis of the RF packet data payload. This payload contains the foot pressure profile based on the current variable pressure following the 6-degrees of freedom motion. This is structured as follows: |0x10|start|F1|F2|F3|F4|Ax|Ay|Az|Pi|Yi|Ri|XOR checksum|.

The IEEE 802.15.4 standard specifies a maximum packet size of 127 bytes and the Time Synchronized Mesh Protocol (TSMP) reserves 47 Bytes for operation, leaving 80 Bytes for payload. The IEEE 802.15.4 is compliant with the 2.4 GHz Industrial, Scientific, and Medical (ISM) band Radio Frequency (RF) transceiver.

The RF module contains a complete 802.15.4 Physical layer (PHY) modem designed for the IEEE 802.15.4 wireless standard which supports peer-to-peer, star, and mesh networking. It is combined with a MCU to create the required wireless RF data link and network. The IEEE 802.15.4 transceiver supports 250 kbps O-QPSK data in 5.0 MHz channels and full spread-spectrum encode and decode.

In some embodiments, control, reading of status, writing of data, and reading of data is done through the sensing system node device's RF transceiver interface port. The sensing system node device's MPU accesses the sensing system node device's RF transceiver through interface 'transactions' in which multiple bursts of byte-long data are transmitted on the interface bus. Each transaction is three or more bursts long, depending on the transaction type. Transactions are always read accesses or write accesses to register addresses. The associated data for any single register access is always 16 bits in length.

In some embodiments, control of the foot pressure/6-degrees of freedom motion collecting node's RF transceiver and data transfers are accomplished by means of a Serial Peripheral Interface (SPI). Although the normal SPI protocol is based on 8-bit transfers, the foot pressure/6-degrees of freedom motion collecting collector node's RF transceiver imposes a higher level transaction protocol that is based on multiple 8-bit transfers per transaction. A singular SPI read or write transaction consists of an 8-bit header transfer followed by two 8-bit data transfers.

The header denotes access type and register address. The following bytes are read or write data. The SPI also supports recursive 'data burst' transactions in which additional data transfers can occur. The recursive mode is primarily intended for Packet RAM access and fast configuration of the foot pressure/6-degrees of freedom motion collecting node's RF In some embodiments, all foot pressure sensor zones are sequentially scanned and the entire process repeats until a reset condition or inactivity power-down mode. The 6-degrees of freedom motion is captured by a serial UART interface to the Inertial Measurement Unit (IMU) from the MCU. The sampling rate for all sensing dimensions is 100-300 Hz which is Ax, Ay, Az, Pitch, Yaw, Roll and which sampled data is stored in IMUBuffer[ ].

A call is made to SPIDryWrite to update the TX packet length field. Next, a call to SPIClearRecieveStatReg is made to clear the status register followed by a call to SPIClearRecieveDataReg to clear the receive data register to make the SPI interface ready for reading or writing. With the SPI interface ready, a call is made to SPISendChar sending a 0×FF character which represents the 1st code byte and then SPIWaitTransferDone is called to verify the send is done.

Figure 5:
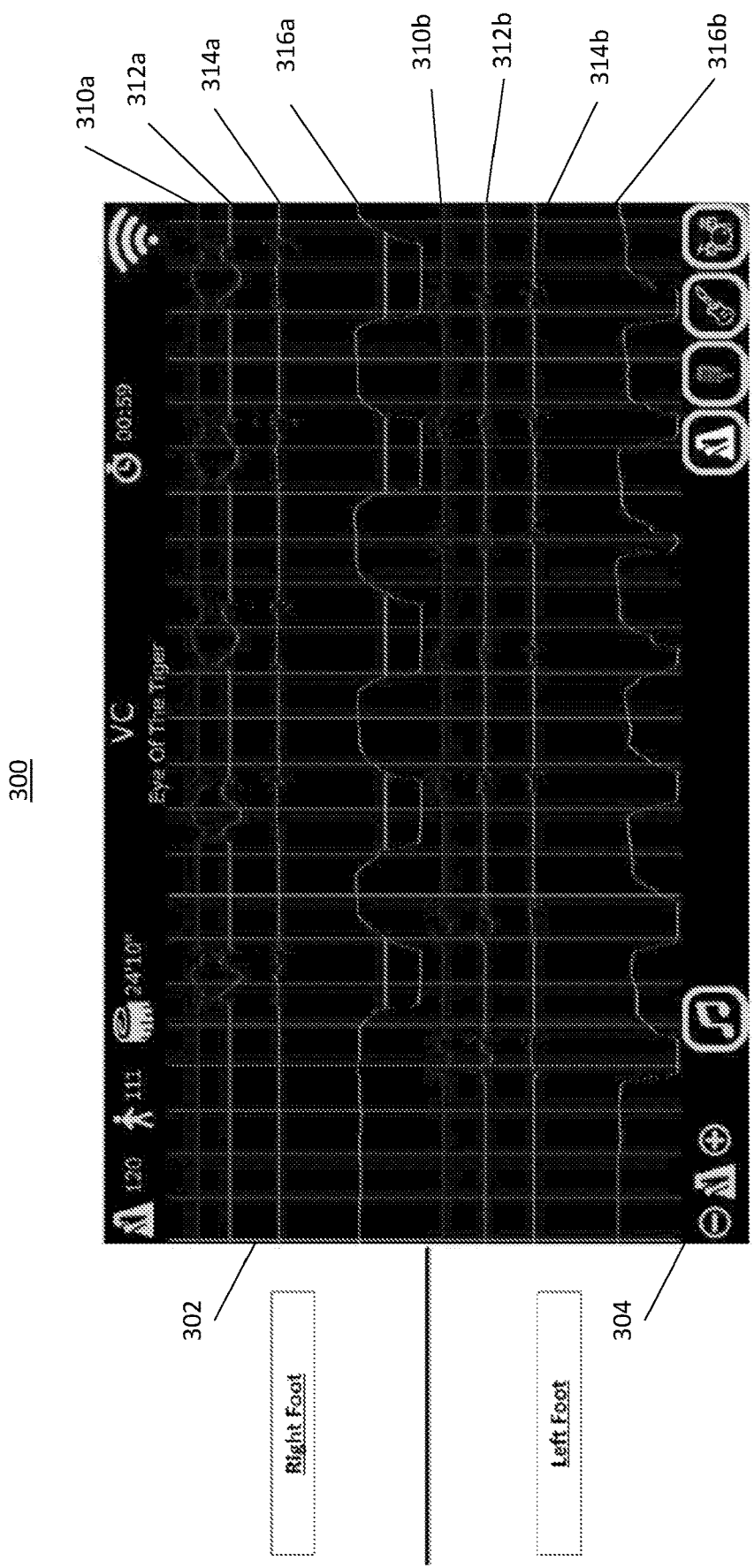
FIG. 5 illustrates an exemplary display of a component of a system for rehabilitation of a user by providing music therapy in accordance with exemplary embodiments of the disclosed subject matter.

FIG. 5 is an exemplary output 300 that may be provided on display 222 of the handheld device. For example, when therapy is provided for a patient's gait, the display output 300 may include a portion for the right foot 302 and a portion for the left foot 304. As a function of time, the display for the right foot includes accelerations $A_x$ 310a, $A_y$ 312a, and $A_z$ 314a, and foot pressure 316a. Similarly, the display for the left foot includes acceleration $A_x$ 310a, $A_y$ 312a, and $A_z$ 314a, and foot pressure 316a.

Classification is understood as the correlation of data, e.g., sensor fused data, feature data, or attribute data to real world events, e.g., activities or disposition of the patient. Typically, the classification is created and performed on the analytics system 108. In some embodiments, the collector 106 has a local copy of some 'templates.' Thus, the incoming sensor data and feature extracted data can be classified at the collector or the analytics system.

Context refers to the circumstances or facts that form the setting for an event, statement, situation, or idea. Context-aware algorithms examine the "who," "what," "when" and "where" related to the environment and time in which the algorithm is executed against certain data. Some context-aware actions include an identity, location, time, and activity being executed. In using contextual information to formulate a deterministic action, context interfaces occur among the patient, the environment, and the music therapy session.

The patient's reaction context to a music therapy session can involve a layer of algorithms that interpret the fused sensor data to infer higher-level information. These algorithms distill the patient reaction context. For example, a patient's bio-mechanical gait sequence is analyzed as it relates to a specific portion of the music therapy session. In one example, "lateral tremor" is the classifier of interest. Accordingly, it is determined that the patient's gait becomes more fluid with less lateral tremor.

Analytics Systems

The analytics systems 108, sometimes referred to as the back end system, store large models/archives and include machine learning/analytics processing, with the models described herein. In some embodiments, a web interface for login to view archived data, and a dashboard is also provided. In some embodiments the analytics system 108 is located on a remote server computer which receives data from the collector 106 running on a handheld unit such as handheld device or tablet 220. It is contemplated that the processing capability needed to perform the analytics and machine learning functions of the analytics system 108 may be also located on the handheld device 220.

Figure 6:
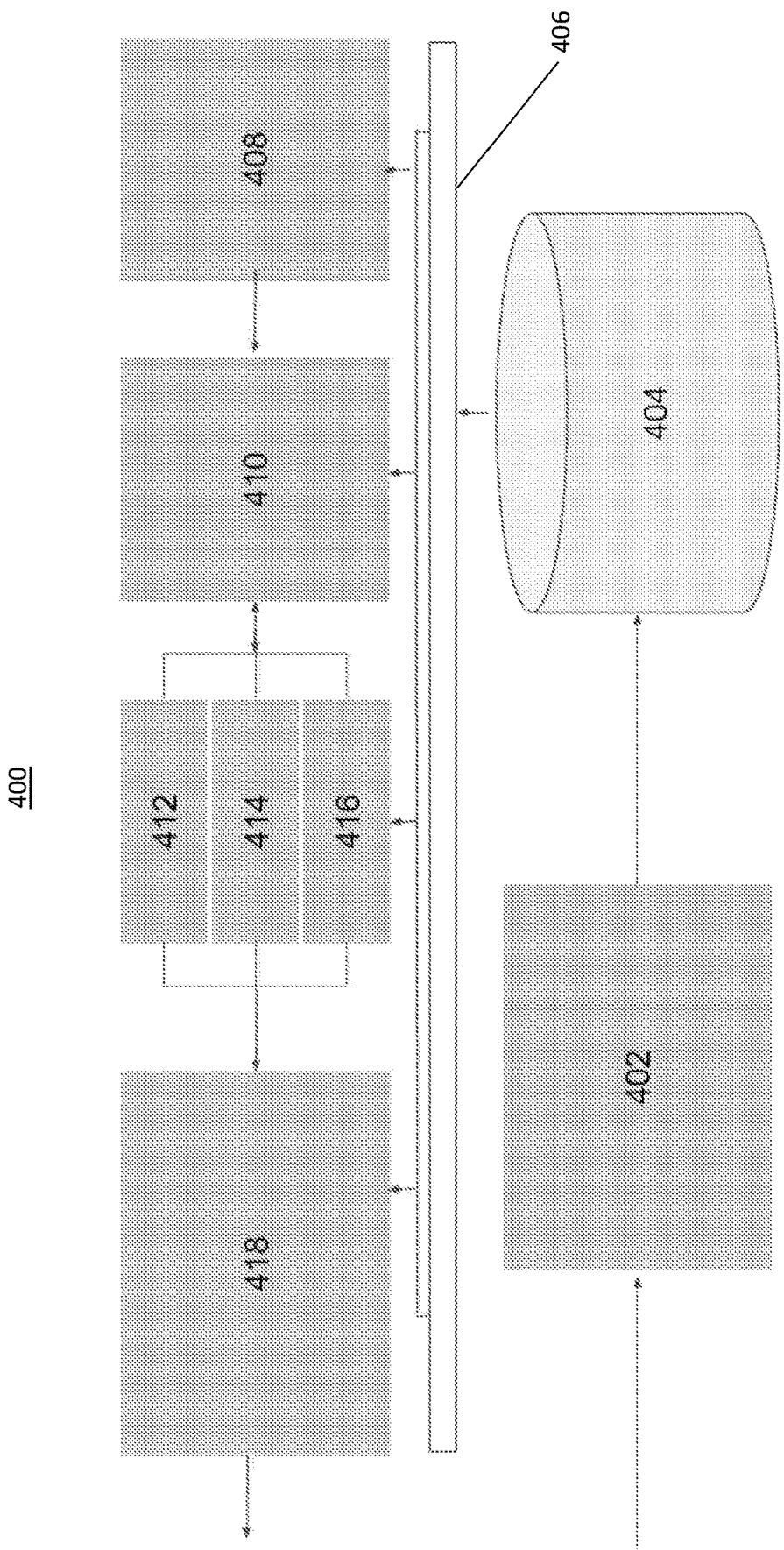
FIG. 6 is a flow diagram for one implementation of an analytics process in accordance with exemplary embodiments of the disclosed subject matter.

Data is transferred from the collector 106 to the analytics systems 108 for analytics processing. As illustrated in FIG. 6, the analytics processing 400 includes a user-interface 402 for receiving data from the collector 106. A database storage 404 receives incoming data from the collector 106 for storage. Training data as well as outputs of the analytics processing, e.g., the ensemble machine learning system 410, may also be stored on storage 404 to facilitate the creation and refinement of the predictive models and classifiers. A data bus 406 allows flow of data through the analytics processing. A training process 408 is performed on training data to derive one or more predictive models. An ensemble machine learning system 410 utilizes the predictive models. The output of the ensemble machine learning system 410 is an aggregation of these predictive models. This aggregated output is also used for classification requirements with template classifiers 412, such as tremor, symmetry, fluidity, or learned biomechanical parameters such as entrainment, initiation, etc. An API 418 connects to the collector and/or music therapy Center. Therapy algorithms 414 and predictive algorithms 416 include multi-layer perceptron neural networks, hidden Markov models, Radal based function networks, Bayesian inference models, etc.

An exemplary application of the systems and methods described herein is analysis of a patient's bio-mechanical gait. The gait sequence is feature-extracted into a series of characteristic features. The presence of these and other features in captured sensor-fused data inform the context detection algorithm if the patient's bio-mechanical gait sequence is valid. Bio-mechanical gait sequence capture requires robust context detection, which is then abstracted over a representative population of music therapy patients.

An example of such an activity is the location of a patient at an instance in time and their response to the music therapy at that time. The recognition and correlation of patient music therapy responses allows for recognition specific patterns of music therapy patient responses. Specific music therapy regimes are then benchmarked and analyzed for performance and efficacy by creating a baseline of music therapy patient responses and correlating them to future music therapy patient responses.

In combination with motion sensing, a distance metric with gait bio-mechanics capture is used to determine patient path trajectory using temporal and spatial variations/deviations between two or more music therapy sessions. From this sensor-fused data capture, features are extracted and classified to label various key patient therapy responses. Further sensor-fused data analysis uses histograms to allow for initial music therapy response pattern detection.

For music therapy session sensor fused data analysis, initially, patient specific Bayesian inference models are used utilizing Markov chains. The states of the chain represent the patient specific response patterns captured from music therapy baseline sessions. The inference is based on knowledge of the patient response pattern appearances at each sample interval and the temporal link to the previous state.

The prediction routine, a Multi-Layer Perceptron Neural Network (MLPNN), uses a directed graph node-based model having a top layer root-node which predicts requirements for reaching a subsequent node and obtaining a patient's sensor-fused data feature vector. This sensor fused data feature vector contains time-series processed motion data, music signature data, and video image data that is specifically significant for further processing. The directed graph, in this case, look like trees that are drawn upside down, where the leaves are at the bottom of the tree and the roots are the root-node. From each node, the routine can go to the left, where left is the left node on the next layer below the top layer which is where the root-node is located, selecting the left sub-node as the next observed node, or to the right where right is the right node on the next layer below the top layer where the root-node is located, and this based on the value of a certain variable whose index is stored in the observed node. If the value is less than the threshold, the routine goes to the left node and if greater, it goes to the right node. These regions, here, left & right, become the predictor spaces.

The model uses two types of input variables: ordered variables and categorical variables. An ordered variable is a value that is compared with a threshold that is also stored in a node. A categorical variable is a discrete value that is tested to see whether it belongs to a certain limited subset of values and stored in a node. This can be applied to various classifications. For example, mild, medium, and severe can be used to describe tremor and is an example of a categorical variable. Conversely, a fine grained range of values or a numerical scale, can be used to similarly describe tremor but in a numerical fashion.

If the categorical variable belongs to the limited set of values, the routine goes to the left node and if not, it goes to the right node. In each node, a pair of entities: variable_index, decision_rule (threshold/subset) are used to make this decision. This pair is called a split which splits on the variable: variable_index.

Once a node is reached, the value assigned to this node is used as the output of the prediction routine. The Multi-Layer Perceptron Neural Network is built recursively, starting from the root node. All training data, feature vectors, and responses, are used to split the root node, as described earlier; where the entities: variable index, decision rule (threshold/subset) segments the prediction regions. In each node the optimum decision rule on the best primary split is found based on gini "purity" criteria for classification and sum of squared errors for regression. The gini index is based on the measure of total variance across a set classes. The gini "purity" criteria referrers to a small gini index value, indicating that a node contains predominantly observations from a single class, which is the desired state.

Once the Multi-Layer Perceptron Neural Network is built, it may be pruned using a cross-validation routine. To avoid model over-fitting, some of the branches of the tree are cut off. This routine may be applied to standalone decisions. One salient property of the decision algorithm (MLPNN), described above, is an ability to compute the relative decisive power and importance of each variable.

The variable importance rating is used to determine the most frequent interaction type for a patient interaction feature vector. The pattern recognition starts with the definition of a decision space suitable to discriminate different categories of music therapy responses and music therapy events. A decision space can be represented by a graph with N dimensions, where N is the number of attributes or measurements considered to represent the music therapy responses and music therapy events. The N attributes compose a feature vector or signature which can be plotted in the graph. After sufficient samples have been inputted, the decision space reveals clusters of music therapy responses and music therapy events belonging to different categories which is used to associate new vectors to these clusters.

The dynamic closed-loop rehabilitation platform music therapy system utilizes several deep learning neural networks for learning and recalling patterns. In one embodiment, a non-linear decision space is built using the adaptive Radial Basis Function (RBF) model generator. New vectors can be calculated using the RBF model and/or with a K-Nearest Neighbor classifier. FIG. 6 illustrates the workflow of the machine learning sub-system of the dynamic closed-loop rehabilitation platform music therapy system.

Figure 7:
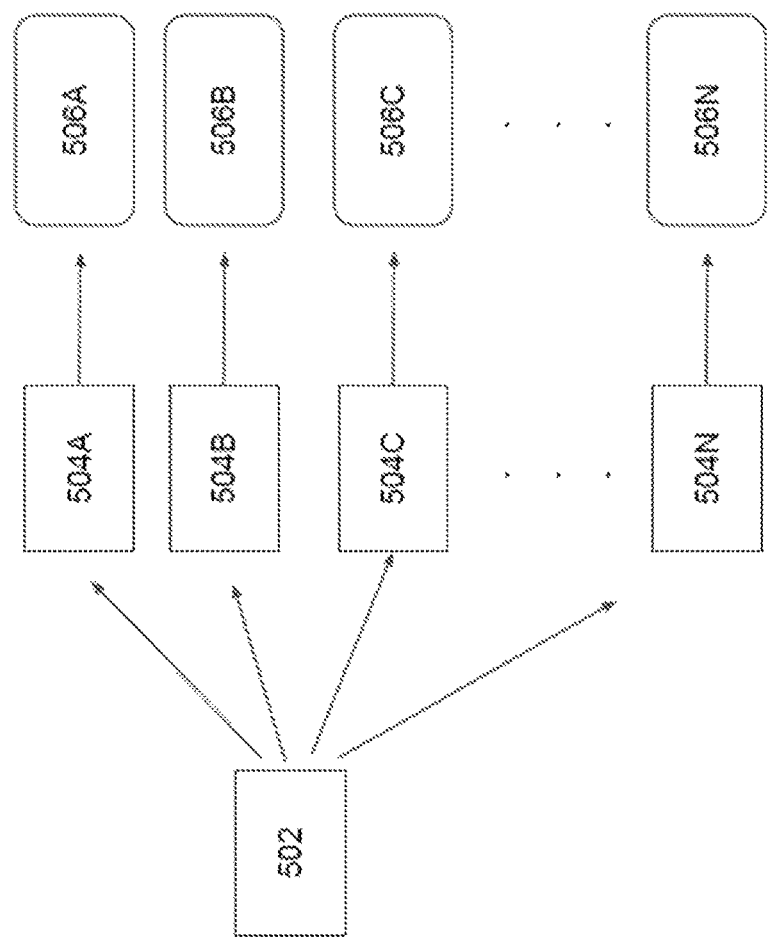
FIGS. 7-10 are flow diagrams for one implementation of a process in accordance with exemplary embodiments of the disclosed subject matter.

FIG. 7 illustrates the supervised training process 408, which includes a number of training samples 502, e.g., inputs would be features such as described in Table 3, above and example outputs will be items such as tremor, asymmetry, and power, the degree of these items, the prediction of changes, classification of how well the patient is recovering. It is understood new outputs are learned as a part of this process. This provides a base for higher levels of abstractions of the predictions and classifications as it is applied to different use cases (e.g. different disease states, combinations with pharmaceuticals, notifications to providers, fitness, and fall prevention). These training samples 502 are run with learning algorithms A1 504*a*, A2 504*b*, A3 504*c* . . . AN 504*n* to derive predictive models in M1 506*a*, M2 506*b*, M3 506*c* . . . MN 506*n*. Exemplary algorithms include Multi-Layer Perceptron Neural Networks, Hidden Markov Models, Radal Based Function Networks, Bayesian inference models.

Figure 8:
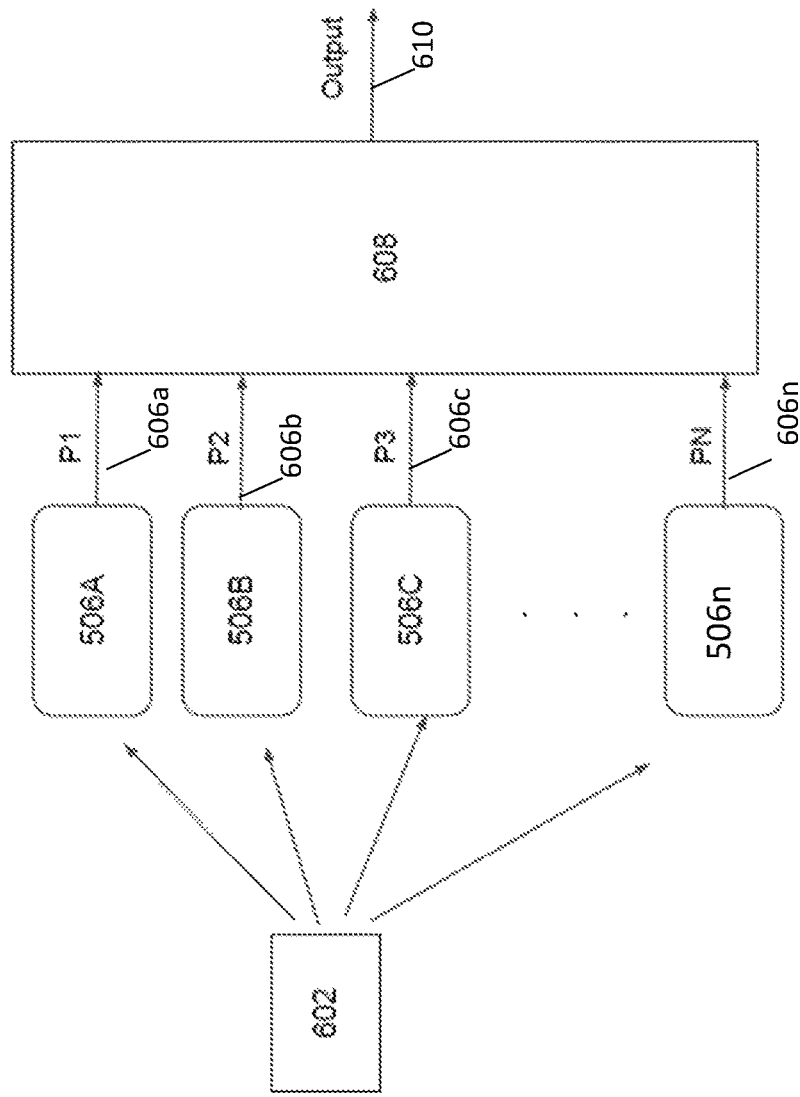

FIG. 8 illustrates the ensemble machine learning system 410, as an aggregation of the predictive models M1 506*a*, M2 506*b*, M3 506*c* . . . MN 506*n* on sample data 602 e.g., feature extracted data, to provide multiple predictive outcome data 606*a*, 606*b*, 606*b* . . . 606*n*. An aggregation layer 608, e.g., including decision rules and voting, is used to derive the output 610, given a plurality of predictive models.

The MR ConvNet system has two layers, where the first layer is a convolutional layer with mean pooling support. The MR ConvNet system second layer is a fully connected layer that supports multinomial logistic regression. Multinomial logistic regression, also called Softmax, is a generalization of logistic regression for handling multiple classes. In the case of logistic regression, the labels are binary.

Softmax is a model that is used to predict the probabilities of the different possible outputs. The following assumes a multiclass classifier with m discrete classes via a Softmax final output layer:

$$Y1 = \text{Softmax}(W11*X1+W12*X2+W13*X3+B1) \quad [1]$$

$$Y2 = \text{Softmax}(W21*X1+W22*X2+W23*X3+B2) \quad [2]$$

$$Y3 = \text{Softmax}(W31*X1+W32*X2+W33*X3+B3) \quad [3]$$

$$Ym = \text{Softmax}(Wm1*X1+Wm2*X2+Wm3*X3+Bm) \quad [4]$$

Figure 9:
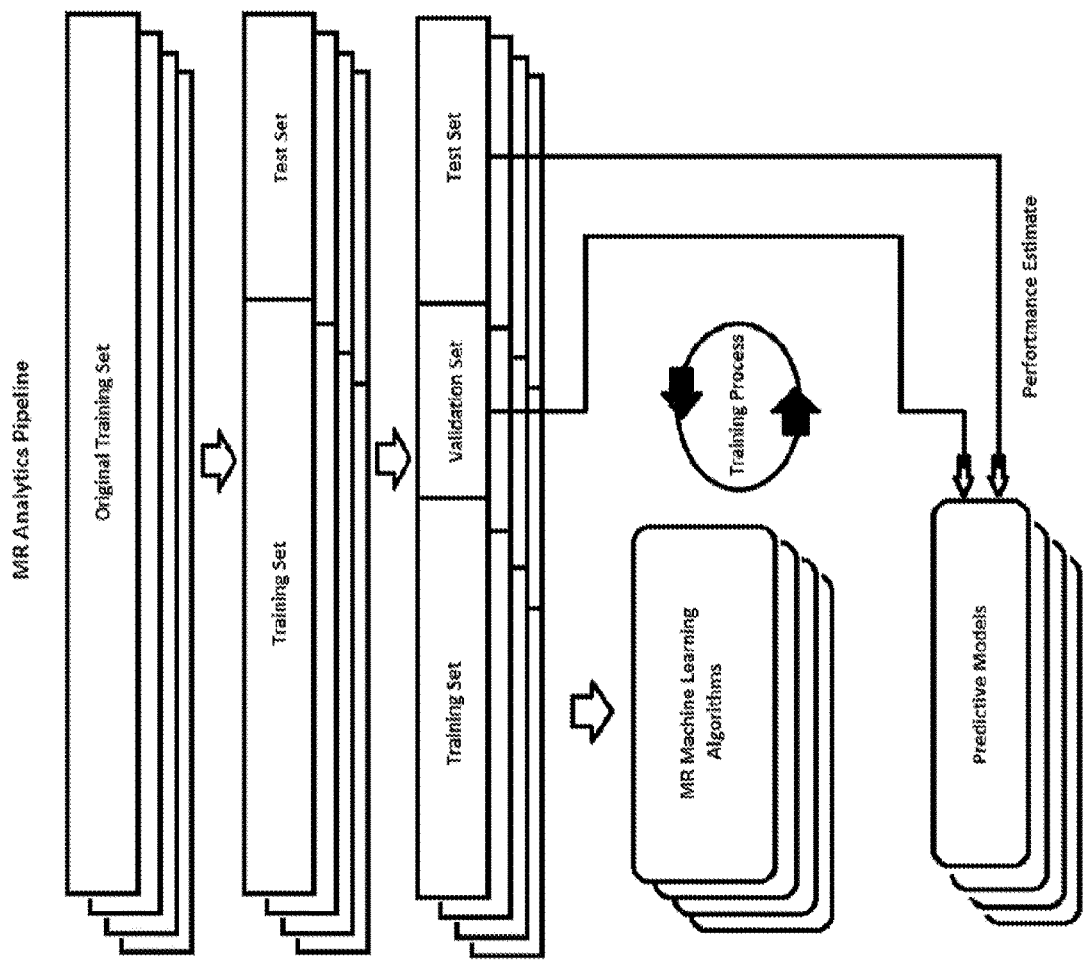

In general: $Y = \text{softmax}(W*X+B)$ [5]

$$\text{Softmax}(X)i = \exp(Xi)/\text{Sum of } \exp(Xj) \text{ from } j=1 \text{ thru } N \quad [6]$$

Where Y=Classifier output; X=Sample input (all scaled (normalized) feature values); W=Weight Matrix. The classifications will, for example, score asymmetry, such as "Moderate Asymmetry score 6 out of 10 (10 high level of asymmetry to 0 for no asymmetry)" or gait fluidity "Gait Fluidity score 8 out of 10 Normal", etc. The Analytics pipelines is illustrated in FIG. 9.

Softmax regression allows for handling multiple classes beyond two. For logistic regression: $P(x)=1/(1+\exp(-Wx))$ where W contains the model parameters that were trained to minimize a cost function. Also, x is the input features vector and $$((x(1),y(1)), \ldots ,(x(i),y(i))) \quad [7]$$

would represent the training set. For multi-class classification, Softmax regression is used where y can take on N different values representing the classes instead of 1 and 0 in the binary case. So for the training set ((x(1), y(1)), . . . ,(x(i), y(i))), y(n) can be any value in the range of 1 through N classes.

Next, p(y=N|x;W) is the probability for each value of i=1, . . . , N. The following mathematically illustrates the Softmax regression process:

$$Y(x)=(p(y=1|x;W),p(y=2|x;W), \ldots p(y=N|x;W)) \quad [8]$$

Where Y(x) is the answer to the hypothesis, that given the input x, output the probability distribution across all classes such that their normalized sum is 1.

The MR ConvNet system convolves every windowed biomechanical data frames, as a vector, with every biomechanical template filter, as a vector, and then generates the responses using a mean pool function which averages the feature responses. The convolution process computes Wx while adding any biases and then passes this to a logistic regression (sigmoid) function.

Next, in the MR ConvNet system's second layer, the sub-sampled biomechanical template filter responses are moved into a two dimensional matrix where each column represents the windowed biomechanical data frames as a vector. The Softmax regression activation process is now initiated using:

$$Y(x)=(1/(\exp(Wx)+\exp(Wx)+ \ldots +\exp(Wx))*(\exp(Wx),\exp(Wx), \ldots ,(\exp(Wx)) \quad [9]$$

The MR ConvNet system is trained with an optimization algorithm, gradient descent where a cost function J(W) is define and will be minimized:

$$J(W)=1/j*((H(t(j)=1),p(y=1|x;W)+H(t(j)=2),\\p(y=2|x;W)+ \ldots +H(t(j),p(y=N|x;W)) \quad [10]$$

Where t(j) are the target classes. This averages all cross-entropies over the j training samples. The cross-entropy function is:

$$H(t(j),p(y=N|x;W)=-t(j)=1)*\log(p(y=1|x;W))+\\t(j)=2)*\log(p(y=2|x;W))+ \ldots +t(j)*p(y=N|x;W) \quad [11]$$

Figure 10:
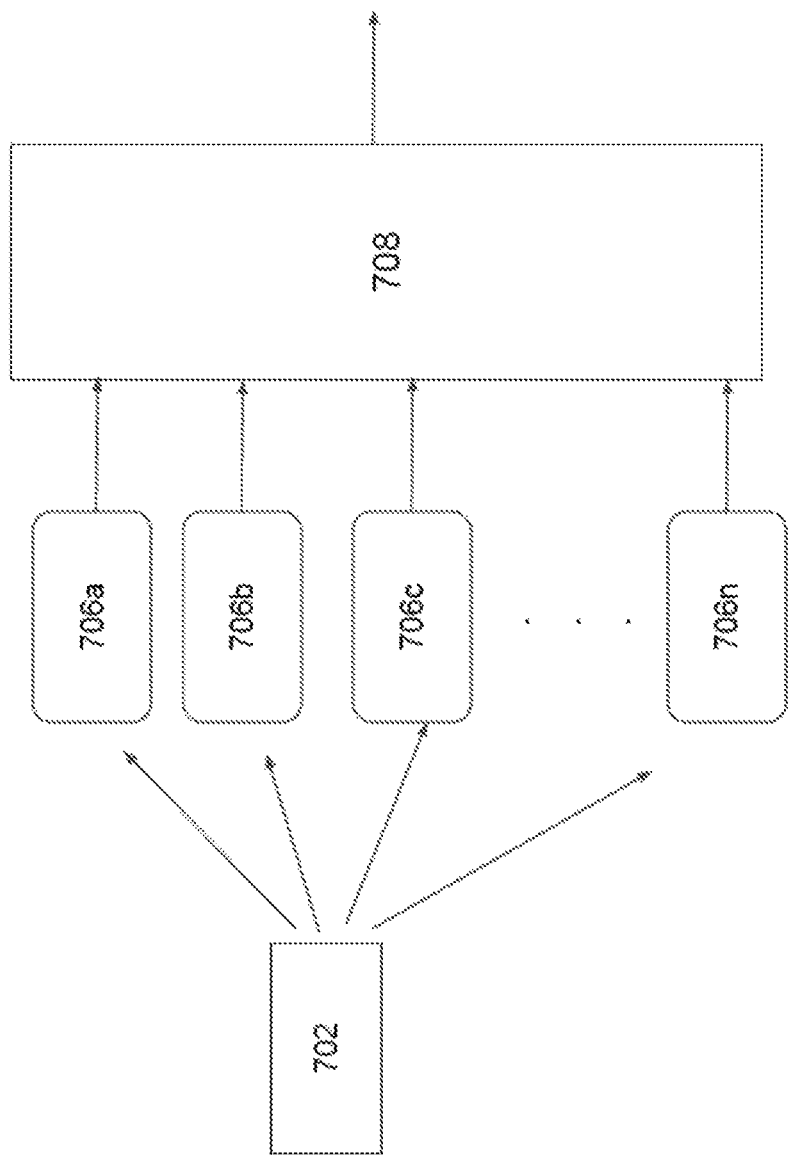

In FIG. 10, the ensemble machine learning system 408 includes a plurality of predictive models, e.g., Template Series 1 (tremor) 706a, Template Series 2, (symmetry) 706b, Template Series 3 (fluidity) 706c . . . additional templates (other learned biomechanical parameters, e.g., entrainment, initiation, etc.) 706n which are applied to conditioned inputs 702, e.g., for example, it could be the following: stride length for right and left features (x1, x2), variance of stride length right and left features (x3, x4), cadence right and left features (x6,x7), variance of cadence right and left features (x8, x9) etc. . . . . this is where sample (x1,x2, . . . xn) are referred to as the Vector X which is input to 702 in the ensemble of ML algorithms. These are conditioned referencing normalized and/or scaled inputs]. The aggregation classifier 708 outputs such information as tremor scale, symmetry scale, fluidity scale, etc.

Music Therapy Center

The music therapy center 110 is the decision making system that runs on processor, such as handheld device or laptop computer 220 of FIG. 2. The music therapy center 110 takes the inputs from the feature—in extracted sensor data at the collector 106, compares them to the defined process for the delivering of the therapy, and then delivers content of auditory stimuli that is played through music delivery system 230.

Embodiments of the invention use contextual information to determine why a situation is happening, then encodes observed actions, which causes a dynamic and modulated change in the system-state, and thus the music therapy session, in a closed-loop manner.

The interactions between the patient and music therapy session provide real-time data for determining music therapy patient context awareness, including motion, posture, strides, and gait reaction. After input data is collected by the sensing nodes (at the sensors), embedded nodes process the context-aware data (at edge processing), and provide immediate dynamic action and/or transmit the data to the analytics systems 108, e.g., an elastic network-based processing cloud environment for storage and further processing and analysis.

Based on inputs, the program will take any existing song content, alter the cadence, major/minor chords, meter and musical cues (e.g., melodic, harmonic, rhythmic and force cues). The system can overlay a metronome on existing songs. The song content can be beat mapped (e.g., if W in response to AV or MP3 file) or in MIDI format so that the precise knowledge of when the beat occurs can be used to calculate the entrainment potential. The sensors on the patient can be configured to provide haptic/vibration feedback pulsing at the music content.

EXAMPLES

Figure 11:
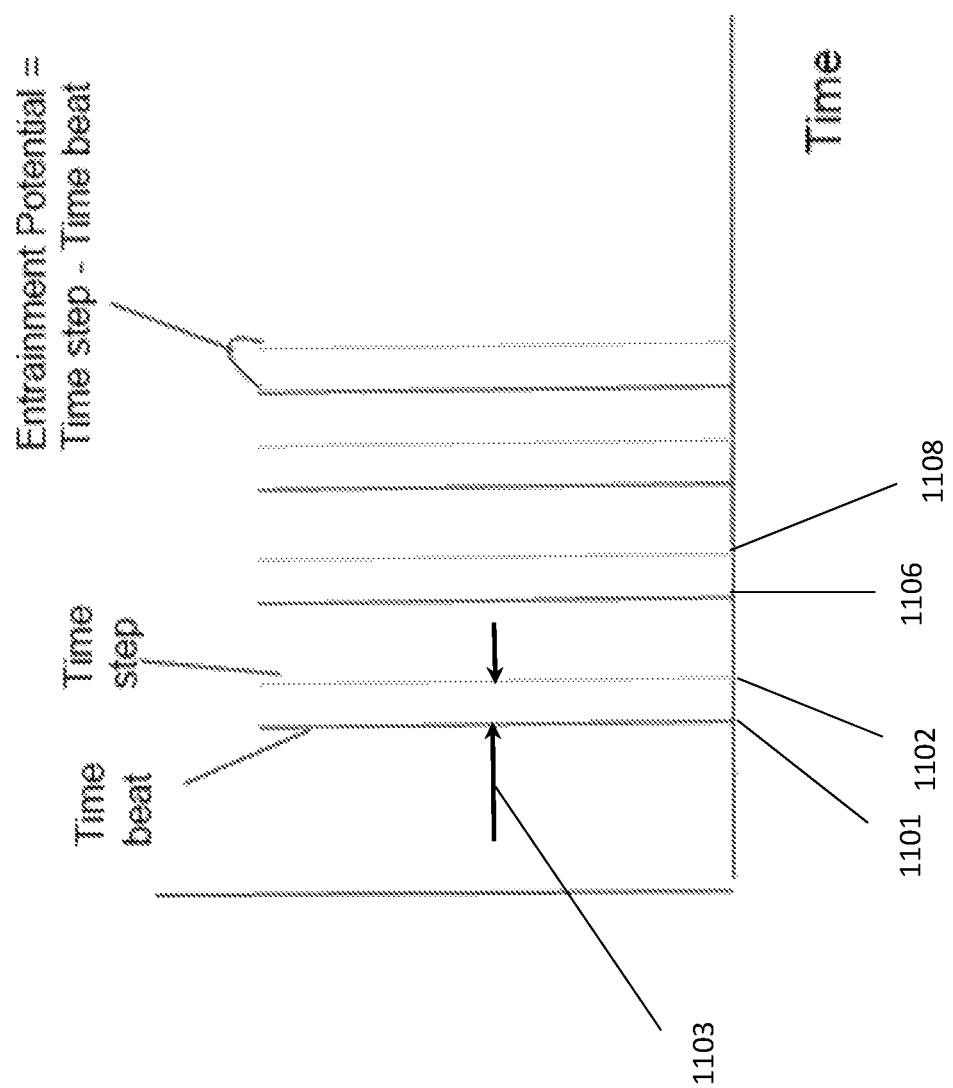
FIG. 11 is a time plot illustrating music and physical movement of the patient in accordance with exemplary embodiments of the disclosed subject matter.

An exemplary application of the method is described herein. Gait training analyzes the real-time relationship between the beats of the music being played for the patient and the individual steps taken by the patient in response to those particular beats of music. As discussed above, gating analysis is used to determine a window of data that repeats, with some variation, with each step or repetitive movement. In some embodiments, the beginning of the window is determined as the time when the heel strike pressure exceeds a threshold (or other sensor parameter.) FIG. 11 is an exemplary time plot illustrating the beats of music, "time beats," and the steps taken by the patient, "time step." Thus the onset time in this case is associated with the "time step." In particular, the plot illustrates a time beat 1101 of the music at time Time Beat 1. After a duration of time, the patient takes a step in response to time beat 1001, i.e., time step 1102, at time Time Step 1. The entrainment potential 1103 represents the delay (if any) between Time Beat 1 and Time Step 1.

Figure 12:
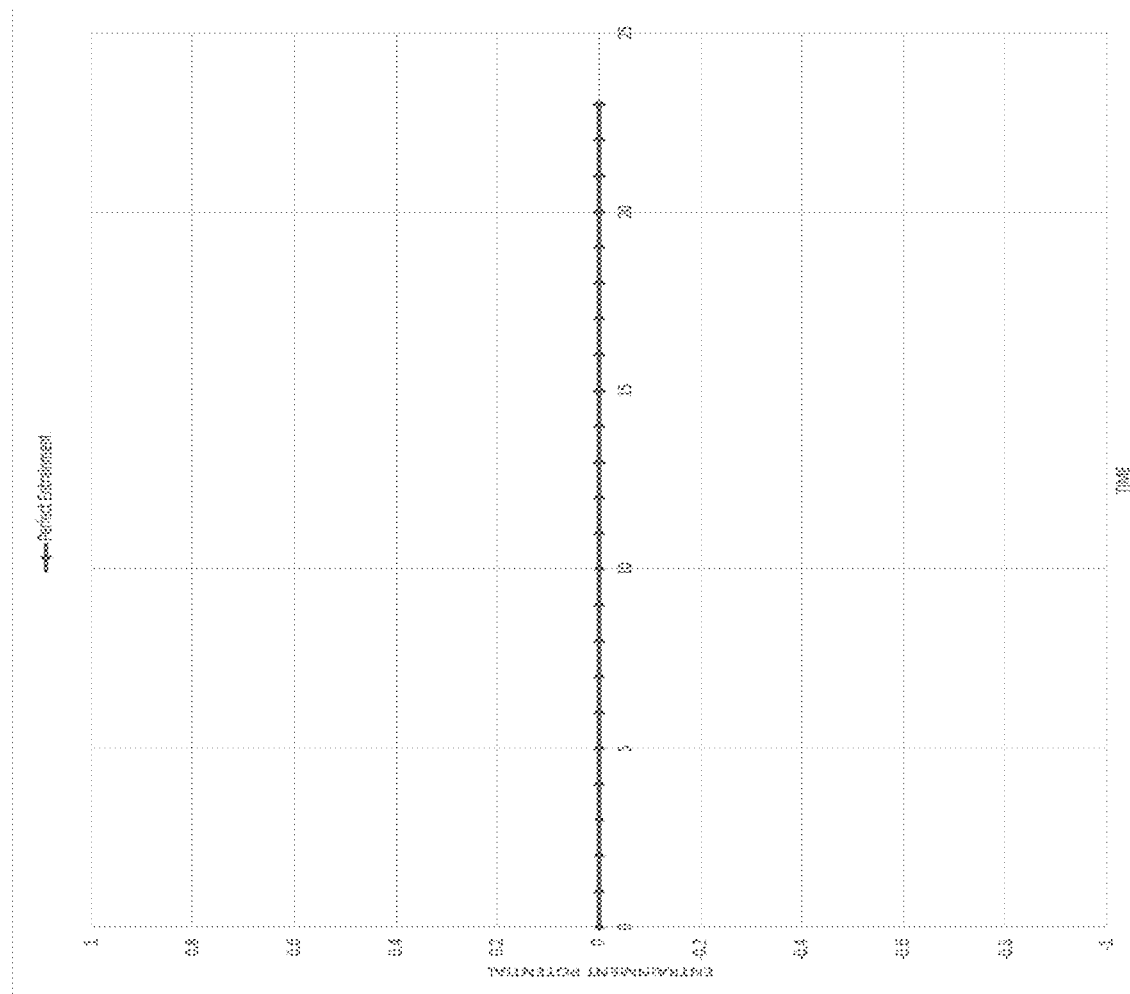
FIGS. 12-13 illustrate a patient response in accordance with exemplary embodiments of the disclosed subject matter.
Figure 13:
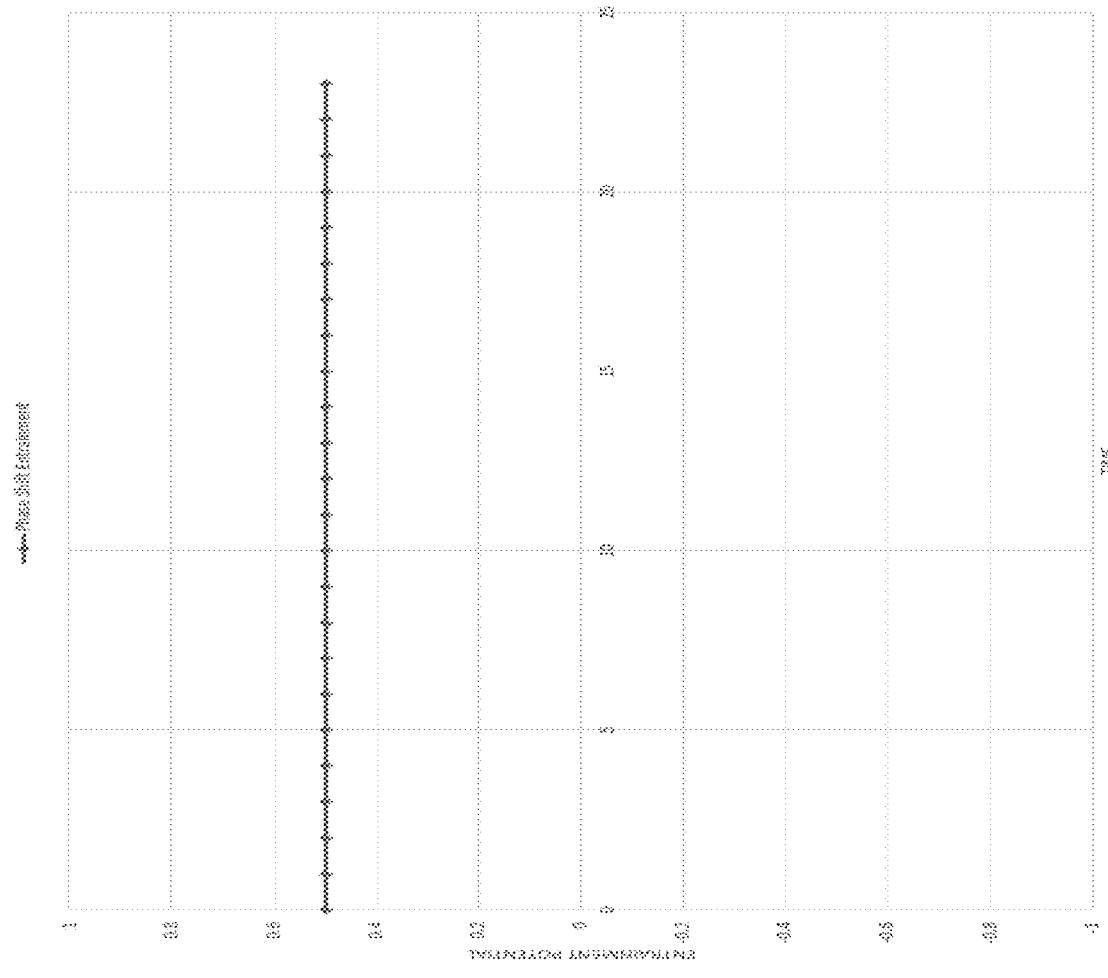

FIGS. 12-13 illustrate examples of entrainment of a patient's gait by use of the system described herein. FIG. 12 illustrates a "perfect" entrainment, e.g., a constant entrainment potential of zero. This occurs when there is no delay, or negligible delay, between the time beat and the associated time step taken in response to the time beat. FIG. 13 illustrates a phase-shift entrainment, e.g., a condition in which the entrainment potential is non-zero, but remains constant, or with minimal variation, over time. This occurs when there is a consistent delay, within tolerances, between the time beat and the time step over time.

With continued reference to FIG. 11, an EP Ratio is calculated as a ratio of the time duration between time beats to the time duration between time steps:

$$EP\ Ratio = \frac{Time\ Beat\ 2 - Time\ Beat\ 1}{Time\ Step\ 2 - Time\ Step\ 1} \quad [6]$$

Where Time Beat 1 1101 corresponds to the time of a first music beat, and Time Step 1 1102 corresponds to the time of the patient's step in response to Time Beat 1. Time Beat 2 1106 corresponds to the time of a second music beat, and Time Step 2 1108 corresponds to the time of the patient's step in response to Time Beat 2. The goal is for an EP Ratio=1 or EP Ratio/Factor=1. The Factor is determined as follows:

$$2^{round\left(log2\left(\frac{Time\ Step\ 2 - Time\ Step\ 1}{Time\ Beat\ 2 - Time\ Beat\ 1}\right)\right)} = Factor \quad [7]$$

Figure 14:
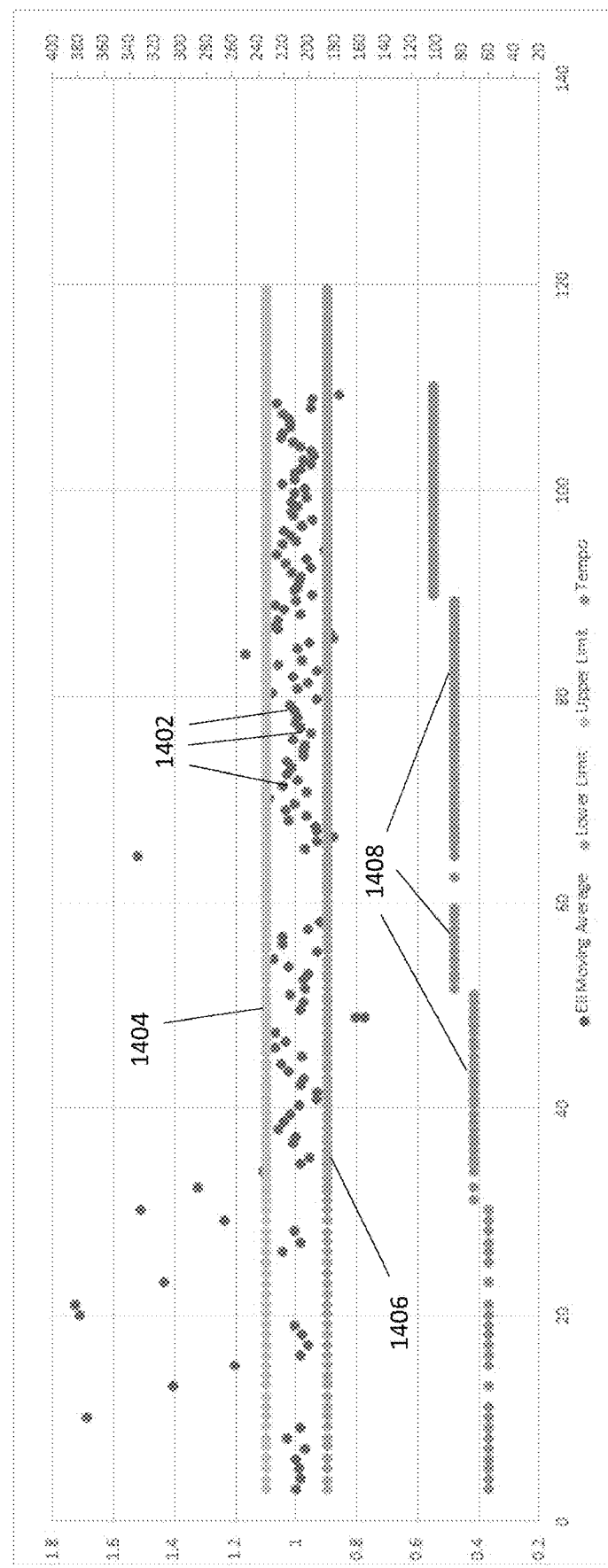
FIGS. 14-15 illustrate a patient response in accordance with exemplary embodiments of the disclosed subject matter.
Figure 15:
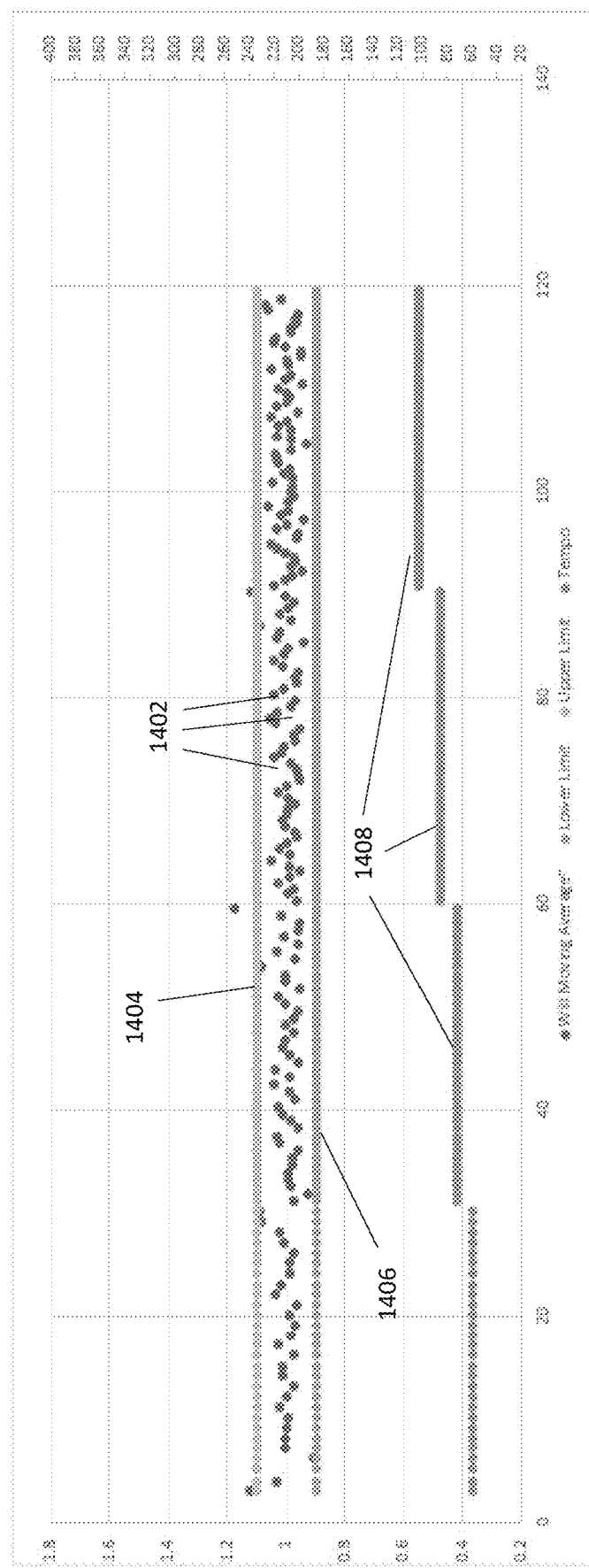

This factor allows the subdivision of beats to happen or for someone to step every 3 beats or 3 out of every 4. It can provide flexibility for different scenarios FIGS. 14 and 15 illustrate the entrainment response over time of a patient using techniques described herein. FIG. 14 (Left Y-axis:EP Ratio; Right Y-axis:Beats Per Minute; X-axis:time) illustrates a scattering of dots 1402 which represent the averages of the EP Ratio of a first patient's gait. The graph illustrates an upper limit 1404 of +0.1 and a lower limit 1406 of −0.1. The lines 1408 illustrate the tempo over time (starting at 60 beats per minute), increasing in steps to 100 bpm). FIG. 14 illustrates that the EP Ratio remains near 1 (±0.1) as the tempo is increased from 60 bpm to 100 bpm. FIG. 15 illustrates the EP ratio of a second patient's gait, in which the EP Ratio also remains near 1 (±0.1) as the tempo is increased from 60 bpm to 100 bpm.

Figure 16:
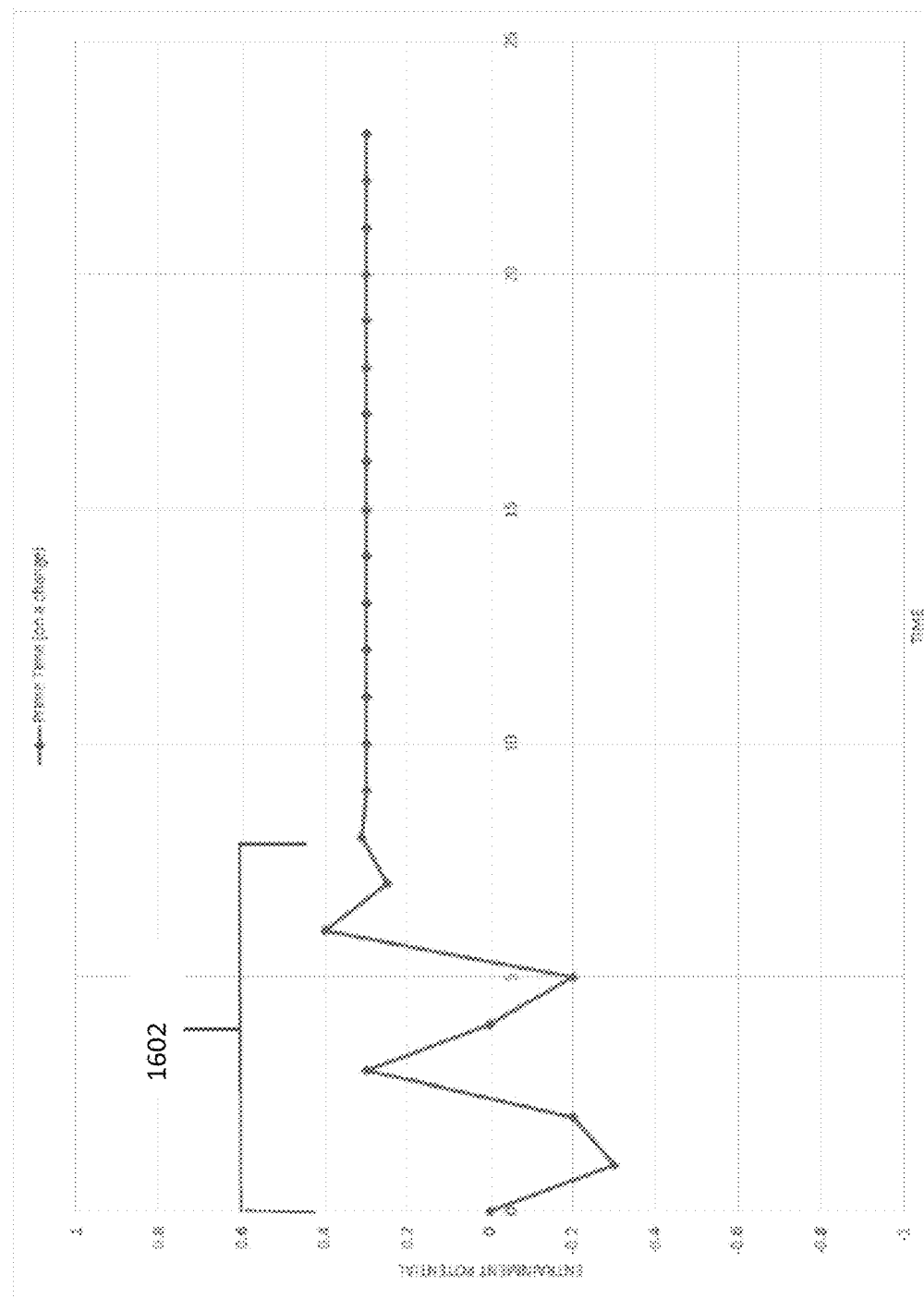
FIGS. 16-17 illustrate a patient response in accordance with exemplary embodiments of the disclosed subject matter.
Figure 17:
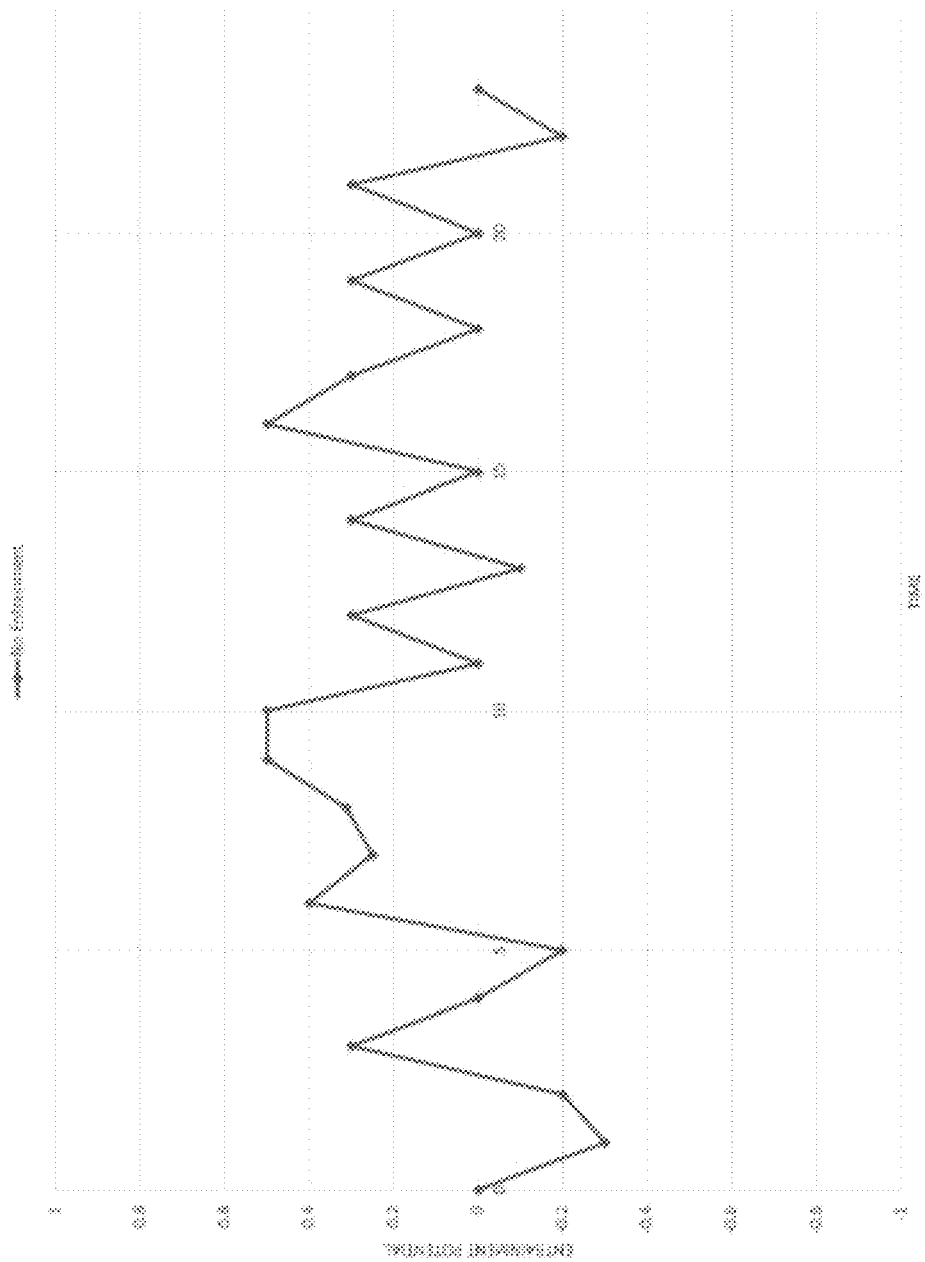

FIGS. 16 and 17 (Y-axis:Entrainment potential, X-axis: Time) illustrate two patients' responses to a change in the time beats (e.g., change in tempo) and/or change to the chords, change in haptic feedback, change in cueing of the feet (e.g., left-right, or left-right-cane cueing), etc. FIG. 16 shows a time based plot in which the patient's gait equilibrates with "perfect entrainment" (constant zero or negligible entrainment potential), or a constant phase-shifted entrainment potential. As illustrated in the figure, it takes a certain period of time, prime time 1602, until equilibration occurs. FIG. 17 illustrates a time-based plot in which the patient's gait does not equilibrate, e.g., does not reach perfect entrainment or a constant phase-shifted entrainment potential after a change to the time beats. Prime time is useful because it represents a set of data that is separate from measuring the accuracy of entrainment. The prime time parameter can also be used to screen future songs for suitability. For example, when patients exhibit a longer prime time value when a music piece is used, such music piece is less capable for therapy.

Figure 18:
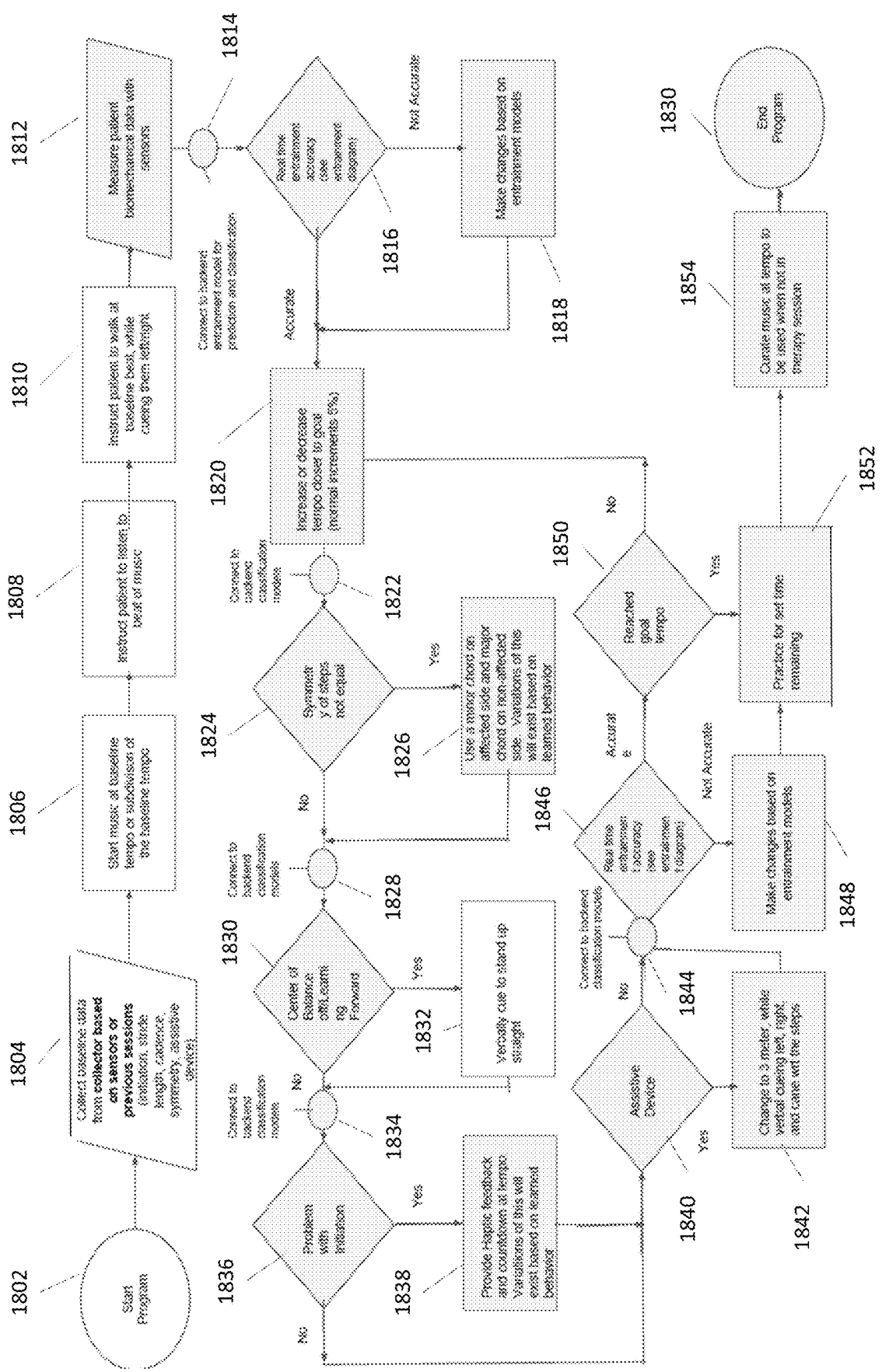
FIG. 18 illustrates an implementation of a technique for gait training of a patient in accordance with exemplary embodiments of the disclosed subject matter.

FIG. 18 illustrates a technique useful for gait training, wherein the repetitive movement refers to the steps taken by the patient while walking. Gait training is adapted to individual patient populations, diagnosis, and conditions to deliver personalized and individualized music interventions. Based on the inputs, the program changes the content, cadence, major/minor chords, meter, and musical cues (e.g., melodic, harmonic, and force cues) where applicable. The program can make selections of music by using date of birth, listed music preferences, and entraining tempo to provide a playlist of passive music to use on a regular basis. The key inputs for gait training are cadence, symmetry and stride length of the user executing the physical activity, e.g., walking. The program uses connected hardware to provide haptic/vibration feedback at the BPM of the music. The appropriate populations for gait training include patients with traumatic brain injury (TBI), stroke, Parkinson's, MS and aging.

The method starts at step 1802. At step 1804, biomechanical data is received at the collector 106 based on data from sensors, e.g., sensors 200, 206, 208. Biomechanical data includes initiation, stride length, cadence, symmetry, data about assistive device, or other such patient feature sets that were stored and generated by the analytics systems 108. Exemplary biomechanical data parameters are listed in Table 1, 2, and 3 above. The baseline condition is determined from a one or more sources of data. First, the patient's gait without any music being played is sensed. Sensor and feature data regarding the patient's initiation, stride length, cadence, symmetry, data about assistive device, etc. comprise the patient's baseline biomechanical data for a therapy session. Second, sensor data from previous sessions of the same patient, as well as any higher level classification data from analytics system 108 comprise the patient's historical data. Third, sensor data and higher level classification data for other similarly-situated patients comprise population data. Thus, the Baseline condition can include data from one or more of (a) the patient's baseline biomechanical data for a therapy session, (b) data from the patient's previous sessions, and (c) population data. The baseline beat tempo is then selected from the baseline condition. For example, a baseline beat tempo can be selected to match the current cadence of the patient prior to playing music. Alternatively, the baseline beat tempo can be selected as a fraction or multiple of the current cadence of the patient. As another alternative, the baseline tempo can be selected to match the baseline beat tempo used in the same patient's previous session. As yet another alternative, the baseline beat tempo can be selected based on baseline beat tempos used for other patients with similar physical conditions. Finally, the baseline beat tempo can be selected based on a combination of any of the data described above. A goal beat tempo can also be determined from this data. For example, the goal beat tempo may be selected as a percentage increase in the baseline beat tempo by reference to the improvement exhibited by other similarly situated patients. The tempo is understood to refer to the frequency of beats in the music.

At step 1806, music provided to the patient on music delivery device 230 (e.g., earbuds or headphones, or a speaker) from handheld device 220 is started at baseline tempo or a subdivision of the baseline tempo. In order to supply music to the patient at the baseline tempo, music is having a constant baseline tempo is selected from a database, or existing music is modified, e.g., selectively sped up or slow down, in order to provide beat signals at a constant tempo.

At step 1808, the patient is instructed to listen to the beat of the music. At step 1810, the patient is instructed to walk at the baseline beat tempo, optionally receiving cues as to left and right feet. The patient is instructed to walk such that each step closely matches the beat of the music, e.g., to walk "in time" with the beat tempo. Steps 1806, 1808, and 1810 may be initiated by the therapist, or by audible or visual instructions on the handheld device 220.

At step 1812, the sensors 200, 206, 208 on the patient are used to record patient data, such as heel strike pressure, 6-Dimensional movement, EMG activity, and a video record of patient movement. All sensor data is time-stamped. Data analysis is performed on the time-stamped sensor data including "gate" analysis discussed herein. For example, analysis of the sensor data, e.g., heel strike pressure, is made in order to determine the onset time of each step. Additional data received includes the time associated with each beat signal of the music provided to the patient.

At step 1814, a connection is made to the entrainment model (e.g., the ensemble machine learning system 410 of the analytics system 108 or models downloaded on collector 106 and running on the handheld device 220) for prediction and classification. (It is understood that such connection may be pre-existing or initiated at this time.) Such connection is typically very fast or instantaneous.

At step 1816, an optional entrainment analysis performed at the analytics systems 108 is applied to the sensor data. The entrainment analysis includes the determination of the delay between the beat signal and the onset of each step taken by the patient. As an output from the entrainment analysis, a determination is made regarding the accuracy of the entrainment, e.g., a measure of the instantaneous relationship between the baseline tempo and the patient's step as discussed above regarding the entrainment potential and EP ratio. If the entrainment is not accurate, e.g., entrainment potential is not constant within a tolerance, adjustments are made at step 1818, e.g., speed up or slow down the beat tempo, increase volume, increase sensory input, overlay metronome or other related sound, etc. If the entrainment is accurate, e.g., entrainment potential is constant within a tolerance, an incremental change is made to the tempo at step 1820. For example, the baseline tempo of the music played with handheld device is increased towards a goal tempo, e.g., by 5%.

At step 1822, a connection is made to the entrainment model for prediction and classification. (It is understood that such connection may be pre-existing or initiated at this time.) At step 1824, an optional symmetry analysis is applied to the sensor data. As an output from the symmetry analysis, a determination is made regarding the symmetry of the patient's gait, e.g., how closely the patient's left foot motion matches the patient's right foot motion for stride length, speed, stance phase, swing phase, etc. If the steps are not symmetrical, e.g., below a threshold, adjustments are made at step 1826 to the music broadcast to the patient by the handheld device. A first modification may be made to the music played during movement of one of the patient's feet, and the second modification may be made to music played during movement of the other one of the patient's feet. For example, a minor chord (or increased volume, sensory input, change in tempo, or overlay of sound/metronome) may be played on one side, e.g., an affected side, and a major chord played on the other side, e.g., a non-affected side. The machine learning system 410 predict in advance when symmetry problems are coming based on the 'fingerprint' of the scenarios leading up to it, e.g., by analyzing motions that are indicative of asymmetry. Asymmetry can be determined by comparing the normal gait parameters for someone with their background can determine how affected the side is and compared to other side.

At step 1828, connection is made to the entrainment model for prediction and classification. (It is understood that such connection may be pre-existing or initiated at this time.) At step 1830, an optional center of balance analysis, e.g., whether the patient is leaning forward, is performed on the sensor data. The analysis may be performed by combining outputs of the foot sensors, as well as the video output. As an output from the center of balance analysis, a determination is made regarding whether the patient is leaning forward. If the patient is leaning forward, a cue to the patient to "stand up straight" is made at step 1832, provided by the therapist, or by audible or visual instructions on the handheld device.

At step 1834, a connection is made to the entrainment model for prediction and classification. (It is understood that such connection may be pre-existing or initiated at this time.) At step 1836, an initiation analysis is applied to the sensor data, e.g., patient's exhibits hesitation or difficulty initiating walking. As an output from the initiation analysis, a determination is made regarding the whether the patient exhibits a problem with initiation. If the patient exhibits a problem with initiation, e.g., below a threshold, haptic feedback can be provided to the patient, which may include a countdown at the beat tempo or a countdown prior to the beginning of a song at step 1838.

At step 1840, it is optionally determined whether the patient is using an assistive device, e.g., a cane, crutches, walker, etc. In some embodiments, the handheld device 220 provides a user interface for the patient or therapist to enter information regarding the use of an assistive device. If a cane is present, the analysis is changed to three meter, e.g., cane, right foot, left foot, and cueing by "left foot," "right foot," and "cane," is made at step 1842, provided by the therapist, or by audible or visual instructions on the handheld device.

At step 1844, a connection is made to the entrainment model for prediction and classification. (It is understood that such connection may be pre-existing or initiated at this time.) An optional entrainment analysis 1846 is applied to the sensor data, substantially as described above in step 1816, with the differences noted herein. For example, entrainment may be compared with previous entrainment data from earlier in the session, from previous sessions with the patient, or with data relating to entrainment of other patients. As an output from the entrainment analysis, a determination is made regarding the accuracy of the entrainment, e.g., how closely the patient's gait matches the baseline tempo. If the entrainment is not accurate, adjustments are made at step 1848, substantially in the same manner as described above at step 1818.

If the entrainment is accurate, a determination is made at step 1850 whether the patient is walking at the goal tempo. If the goal tempo is not reached, the method proceeds to step 1820 (described above), so that an incremental change is made to the tempo. For example, the baseline tempo of the music played with handheld device is increased or decreased, e.g., by 5%, towards the goal tempo. If the goal tempo has been reached, the patient may continue the therapy for the remaining time in the session (step 1852). At step 1854, music at the desired tempo to be used when not in therapy session can be curated and left on the device 220 in FIG. 2. This music content is used as homework/practice by the patient between dedicated therapy sessions. At step 827, the program ends.

Is understood that the steps described above and illustrated in FIG. 18 may be performed in a different order than that disclosed. For example, the evaluations at steps 1816, 1824, 1830, 1836, 1840, 1846, and 1850 may be performed at the same time. Moreover, the plurality of connections to the analytics system 108 (e.g., steps 1814, 1822, 1828, 1834, and 1844) may be performed once throughout the therapy session described.

Figure 19:
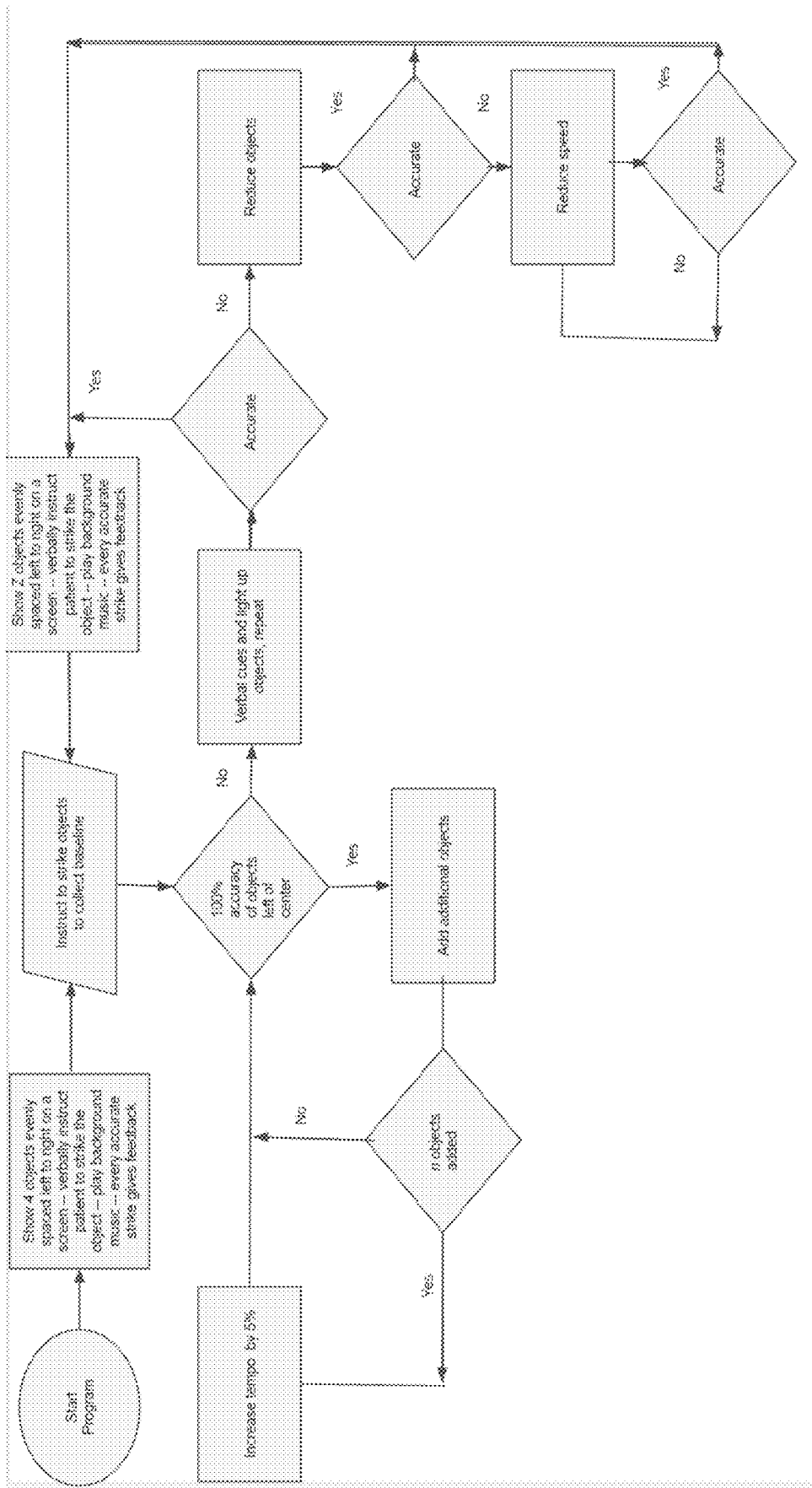
FIG. 19 illustrates an implementation of a technique for neglect training of a patient in accordance with exemplary embodiments of the disclosed subject matter.

FIG. 19 illustrates a technique useful for neglect training. For neglect training, the system and methods described herein use connected hardware to provide haptic/vibration feedback as the patients correctly hit the target. The connected hardware includes a device, video motion capture system or connected bell. All of these devices connect into the system described, vibrate as tapped, and have a speaker to play auditory feedback. For example, the connected bell provides data to the system in the same manner as the sensors 200, e.g., data regarding the bell strike by the patient. The video motion capture system provides video data to the system in the same manner as the video cameras 206. The key inputs for neglect training are information relating to the tracking of movement to a specific location. The program uses connected hardware to provide haptic/vibration feedback as the patient correctly hits the target. The appropriate populations for neglect training include patients with spatial neglect or unilateral visual neglect conditions.

Figure 20:
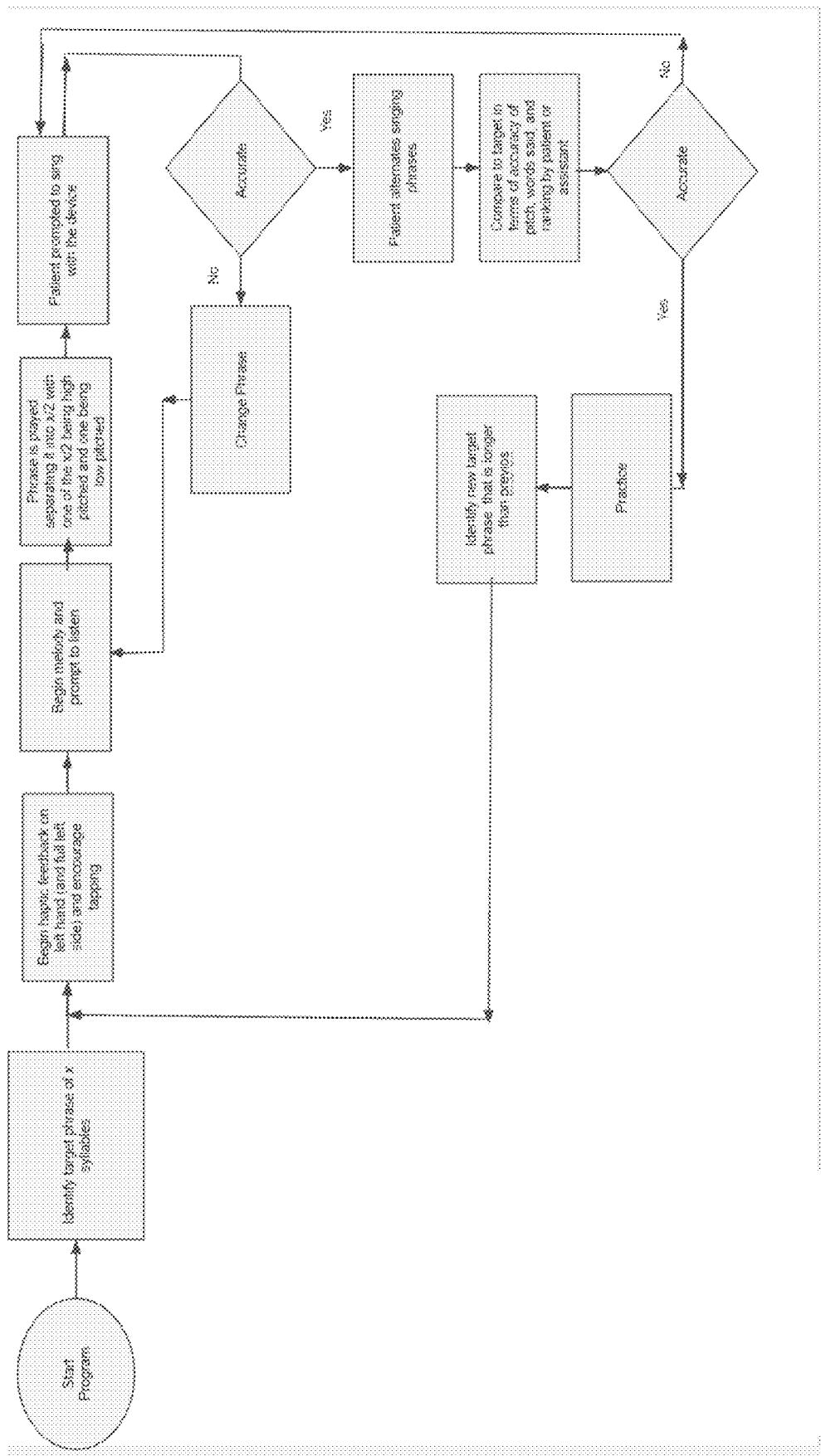
FIG. 20 illustrates an implementation of a technique for intonation training of a patient in accordance with exemplary embodiments of the disclosed subject matter.

The flow diagram illustrated in FIG. 19 for neglect training is substantially identical to the flow illustrated in FIG. 18 for gait training, with the differences noted herein. For example, a baseline test establishes the status of the patient and/or improvement from previous tests. In some embodiments the baseline tests include showing four objects evenly spaced left to right on a screen, e.g., display 222 of handheld device 220. The patient is instructed, either by cues appearing on the display 222 or verbally by a therapist, to strike the object in time with the beats of the background music. As with gait training, the patient is instructed to strike a bell in time with the beat of the background music. Every accurate strike provides feedback. Once the baseline information is collected, a number of objects evenly spaced left to right are displayed on a screen. As above, the patient is instructed to strike the objects in order from left to right in time with the beats of the background music. Every accurate strike provides a feedback. As with gait training, the analytics system 108 evaluates the patient's responses and classifies the responses and provide instructions to add or reduce objects, or increase or decrease tempo of the music to reach a goal tempo FIG. 20 illustrates a technique useful for intonation training. For intonation training, the system and methods described herein relies on voice processing algorithms. The phrases typically chosen are common words in the following categories: bilabials, gutturals, and vowels. The hardware is connected to a patient to provide haptic feedback at the beats per minute to one hand of the patient. The key inputs for intonation training are the tone of voice and words spoken and rhythm of speech. The appropriate populations for intonation training include patients with Broca's aphasia, expressive aphasia, non-fluent aphasia, apraxia, autism spectrum disorder, and Down's syndrome.

The flow diagram illustrated in FIG. 20 for intonation training is substantially identical to the flow illustrated in FIG. 18 for gait training, with the differences noted herein. For example, haptic feedback is provided to one hand of the patient to encourage tapping. The patient is then instructed, either by cues appearing on the display 222 or verbally by a therapist, to listen to the music played. The spoken phrase to be learned is played by separating it into two parts, with the first one of the two parts being high-pitched and the second of the two parts being low pitched. The patient is then instructed, either by cues appearing on the display 222 or verbally by a therapist, to singing the phrase with the device using the two pitches being played. As with gait training, the analytics system 108 evaluates the patient's responses and classifies the responses in terms of accuracy of pitch, words spoken, and ranking by patient or assistant/therapist, and provide instructions to provide alternate phrases and compare responses to targeted speech parameters.

Figure 21:
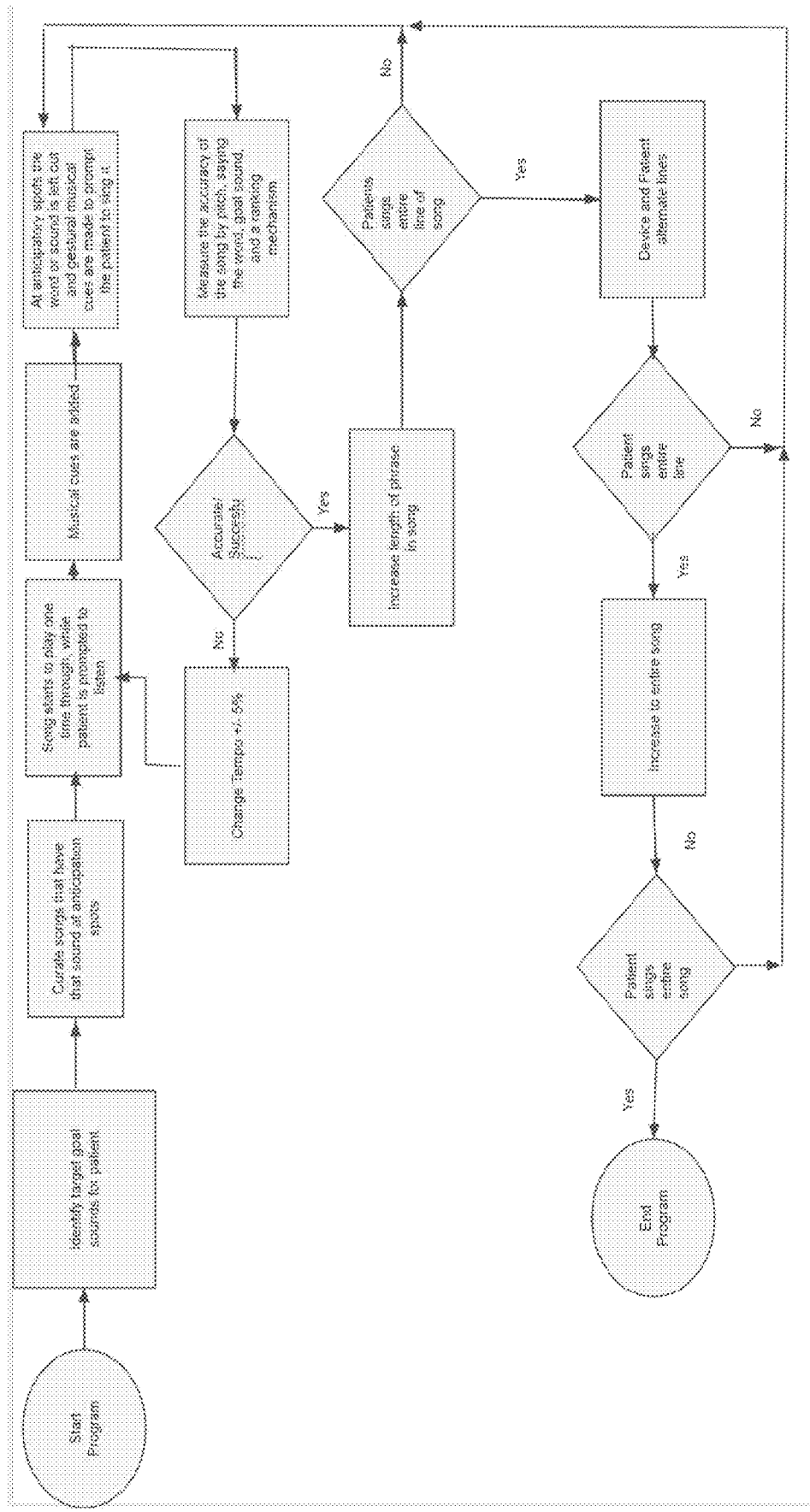
FIG. 21 illustrates an implementation of a technique for musical stimulation training of a patient in accordance with exemplary embodiments of the disclosed subject matter.

FIG. 21 illustrates a technique useful for musical stimulation training. For musical stimulation training, the system and methods described herein relies on voice processing algorithms. Familiar songs are used with an algorithm to separate the anticipatory section out (referred to as an expectancy violation). The hardware includes a speaker for receiving and processing the singing by the patient, and in some embodiments a therapist can manually provide an input regarding singing accuracy. Key inputs are information relating to the tone of voice and words spoken and rhythm of speech, and music preferences. The appropriate populations include patients with Broca's aphasia, non-fluent aphasia, TBI, stroke, and primary progressive aphasia.

The flow diagram illustrated in FIG. 21 for musical stimulation training is substantially identical to the flow illustrated in FIG. 18 for gait training, with the differences noted herein. For example, a song is played for the patient, and the patient instructed either by cues appearing on the display 222 or verbally by a therapist, to listen to the song. Musical cues are added to the song. Subsequently, at anticipatory spots, a word or sound is left out and gestural music cues are played to prompt the patient to sing the missing word or sound. As with gait training, the analytics system 108 evaluates the patient's responses and classifies the responses in terms of accuracy of pitch, words spoken, and ranking by patient or assistant/therapist, and provide instructions to play additional portions of the song in order to improve speech to targeted speech parameters.

Figure 22:
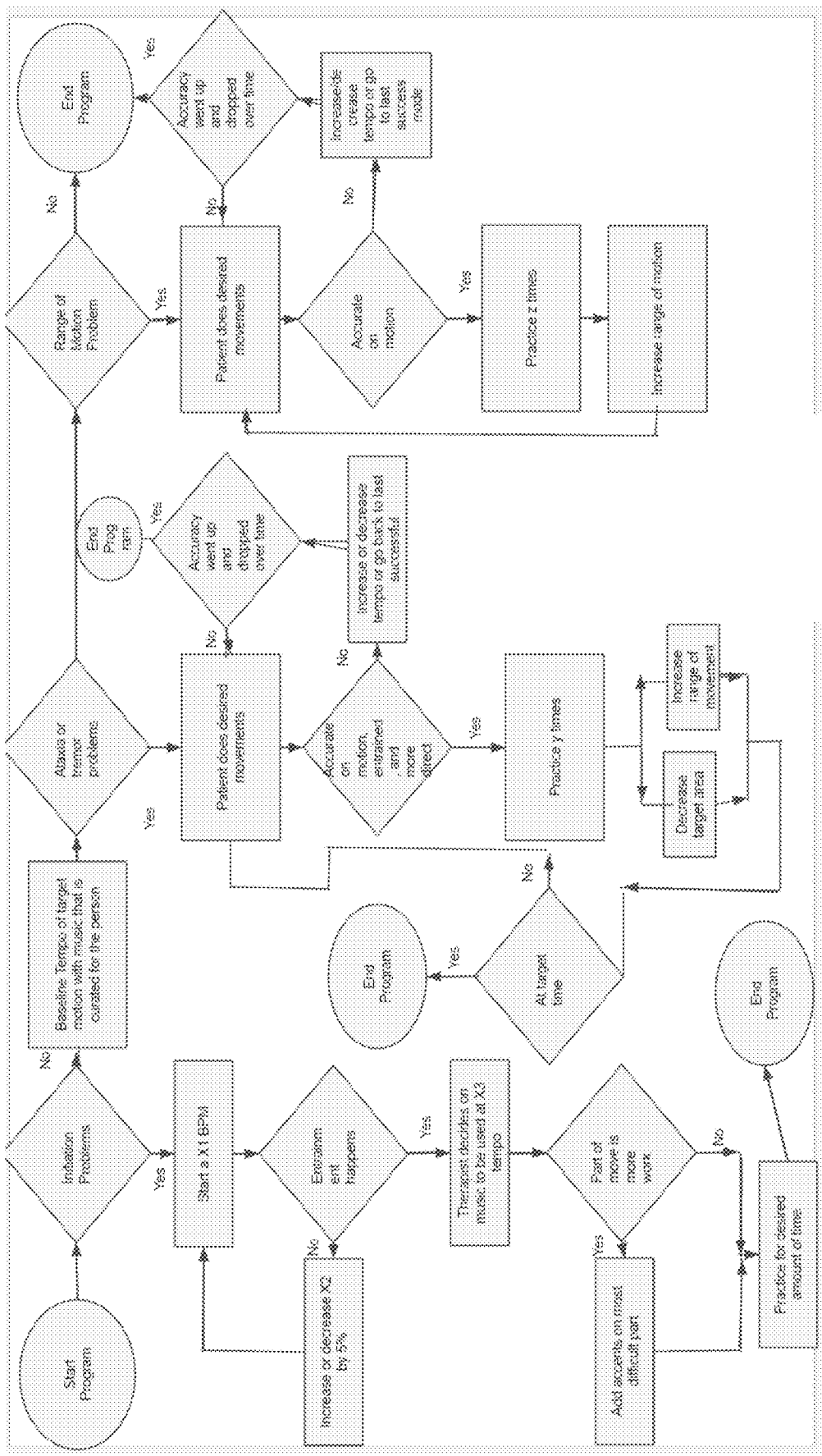
FIG. 22 illustrates an implementation of a technique for gross motor training of a patient in accordance with exemplary embodiments of the disclosed subject matter.

FIG. 22 illustrates a technique useful for gross motor training. For gross motor training, the system and methods described herein are directed to help with ataxia, range of motion or initiation. The more challenging portion of an exercise is musically "accented", e.g., by the use of melodic, harmonic, rhythmic, and/or force cues. Key inputs are information relating to movements in X, Y, and Z-capture via connected hardware or video camera system. The appropriate populations include patients with neurological, orthopedic, strength, endurance, balance, posture, range of motion, TBI, SCI, stroke, and Cerebral Palsy.

The flow diagram illustrated in FIG. 22 for gross motor training is substantially identical to the flow illustrated in FIG. 18 for gait training, with the differences noted herein. As with gait training, the patient's is provided with cues to move in time with the baseline beats of a musical selection. The analytics system 108 evaluates the patient's responses and classifies the responses in terms of accuracy of motion and entrainment as discussed above and provides instructions to increase or decrease the tempo of the music played.

Figure 23:
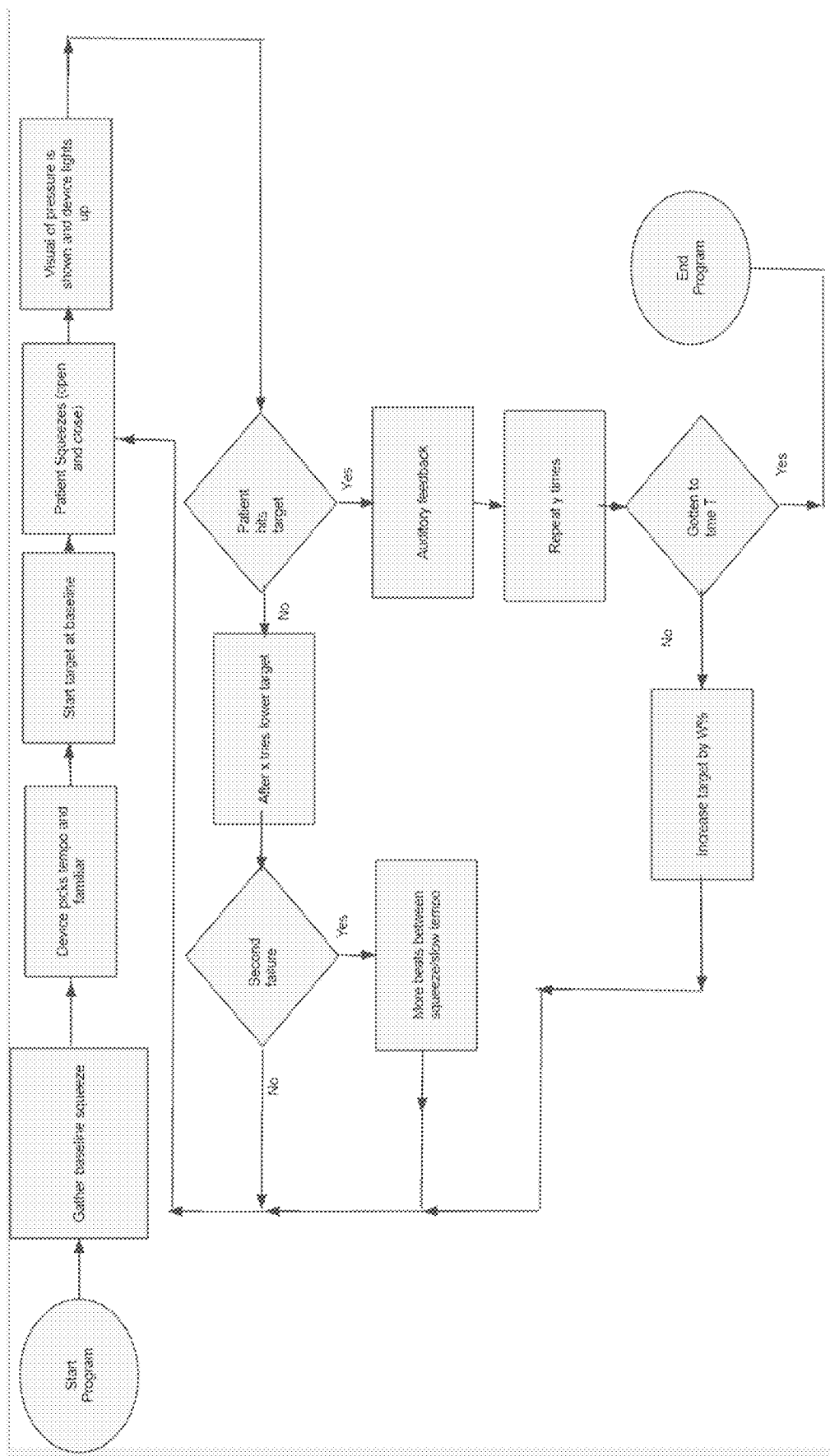
FIG. 23 illustrates an implementation of a technique for grip strength training of a patient in accordance with exemplary embodiments of the disclosed subject matter.

FIG. 23 illustrates a technique useful for grip strength training. For grip strength training, the system and methods described herein rely on sensors associated with the gripper device. The hardware includes a gripper device having pressure sensors, a connected speaker associated with a handheld device 220. Key inputs are the pressure provided by the patient to the gripping device in a similar manner to the heel strike pressure measured by sensor 200. The appropriate populations include patients with neurological, orthopedic, strength, endurance, balance, posture, range of motion, TBI, SCI, stroke, and Cerebral Palsy.

The flow diagram illustrated in FIG. 23, for grip strength training is substantially identical to the flow illustrated in FIG. 18 for gait training, with the differences noted herein. As with gait training, the patient is provided with cues to apply force to the gripping device in time with the baseline beats of a musical selection. The analytics system 108 evaluates the patient's responses and classifies the responses in terms of accuracy of motion and entrainment as discussed above and provides instructions to increase or decrease the tempo of the music played.

Figure 24:
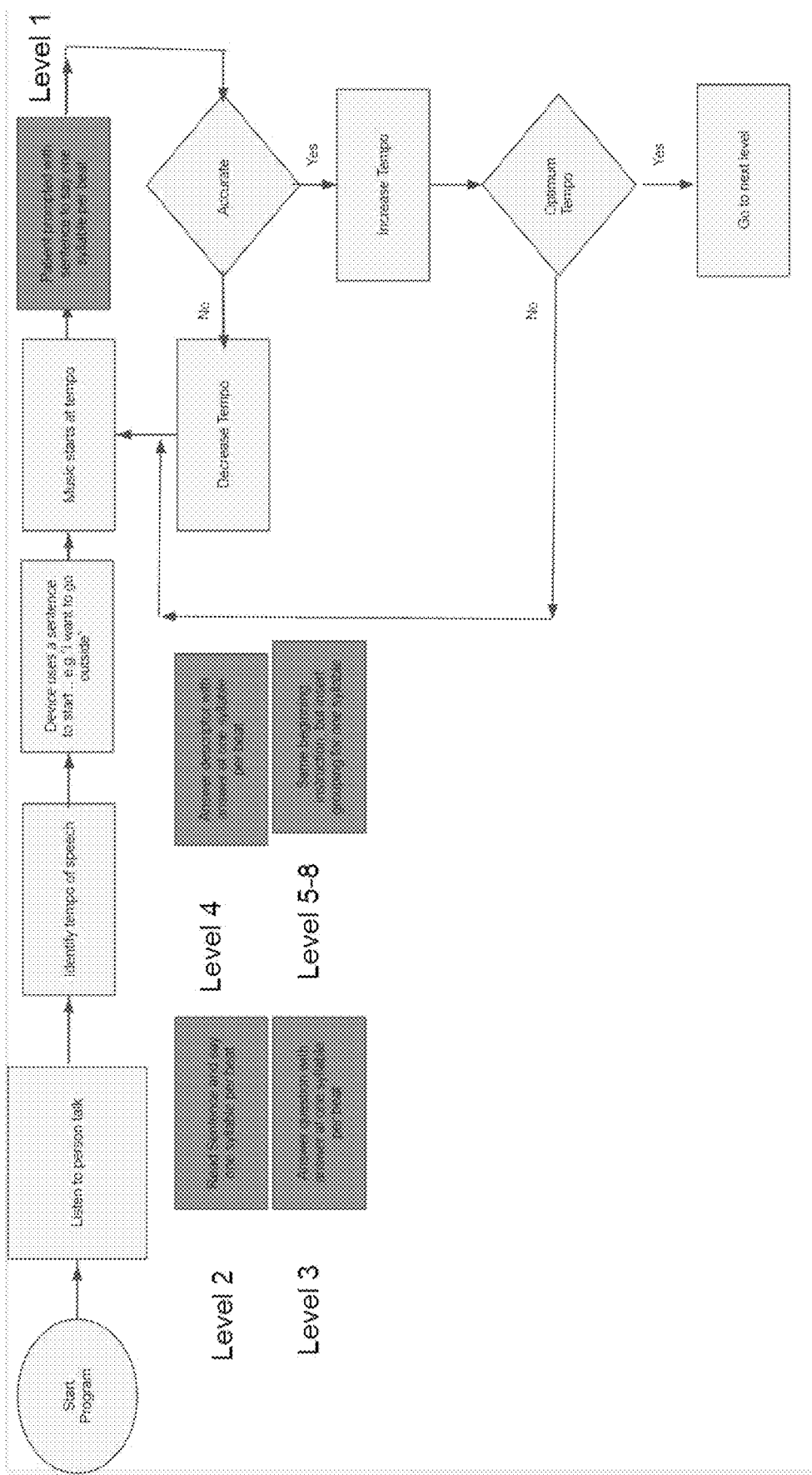
FIG. 24 illustrates an implementation of a technique for speech cueing training of a patient in accordance with exemplary embodiments of the disclosed subject matter.

FIG. 24 illustrates a technique useful for speech cueing training. For speech cueing training, the system and methods described herein relies on voice processing algorithms. The hardware can include a speaker for receiving and processing the singing by the patient, and in some embodiments a therapist can manually provide an input regarding speech accuracy. Key inputs are the tone of voice and words spoken and rhythm of speech, and music preferences. The appropriate populations include patients with robot, word finding and stuttering speech issues.

The flow diagram illustrated in FIG. 24 for speech cueing training is substantially identical to the flow illustrated in FIG. 18 for gait training, with the differences noted herein. As with gait training, the patient is provided with cues to speak a sentence, either by cues appearing on the display 222 or verbally by a therapist, by saying one syllable in time with each beat of a musical selection. The analytics system 108 evaluates the patient's speech and classifies the responses in terms of accuracy of speech and entrainment as discussed above and provides instructions to increase or decrease the tempo of the music played.

Figure 25:
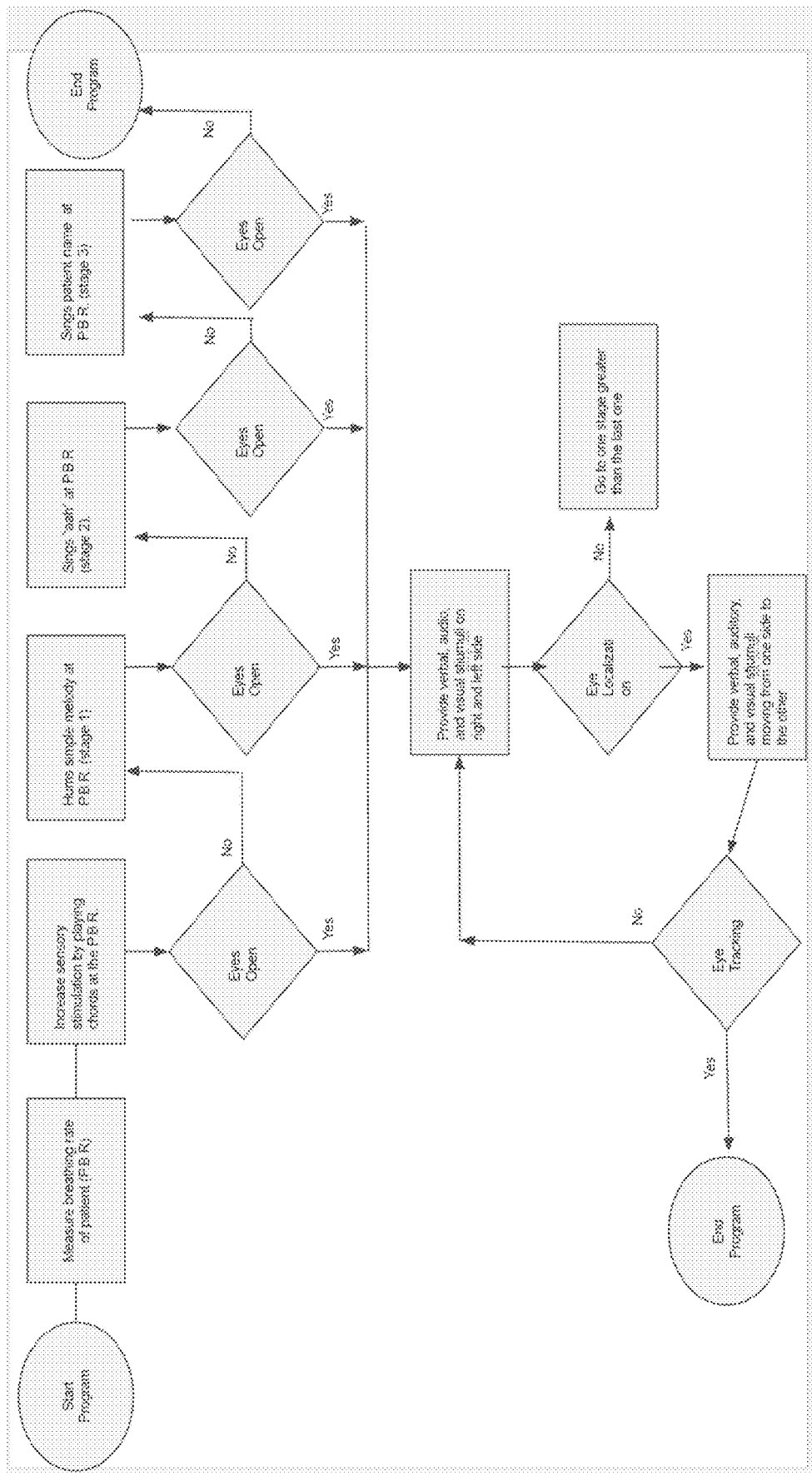
FIG. 25 illustrates an implementation of a technique for training of a minimally conscious patient in accordance with exemplary embodiments of the disclosed subject matter.

FIG. 25 illustrates a technique useful for training of minimally conscious patients. The system and methods described herein rely on an imaging system, such as a 3-D camera, to measure if the eyes of the patient are open, the direction the patient is looking, and the resulting patient pulse or heart rate. The program searches and optimizes for the heart rate, stimulation, respiration rate, eye closure, posturing, and restlessness. The appropriate populations include patients with coma and disorders of consciousness.

The flow diagram illustrated in FIG. 25 for training of minimally conscious patients is substantially identical to the flow illustrated in FIG. 18 for gait training, with the differences noted herein. As with gait training, the patient is provided with increasing stimulation at the breathing rate of the patient (PBR). For example, the patient is first provided with stimulation at the PBR of musical chords and observing whether the patient's eyes are open. If the patient's eyes are not open, the stimulation sequentially increases from humming a simple melody at PBR, to singing "aah" at the PBR, to singing the patient's name at the PBR (or playing a recording of such sounds), and checking at each input whether the patient's eyes are open. The analytics system 108 evaluates the patient's eye tracking and classifies the responses in terms of level of consciousness and provides instructions to change the stimulation.

Figure 26:
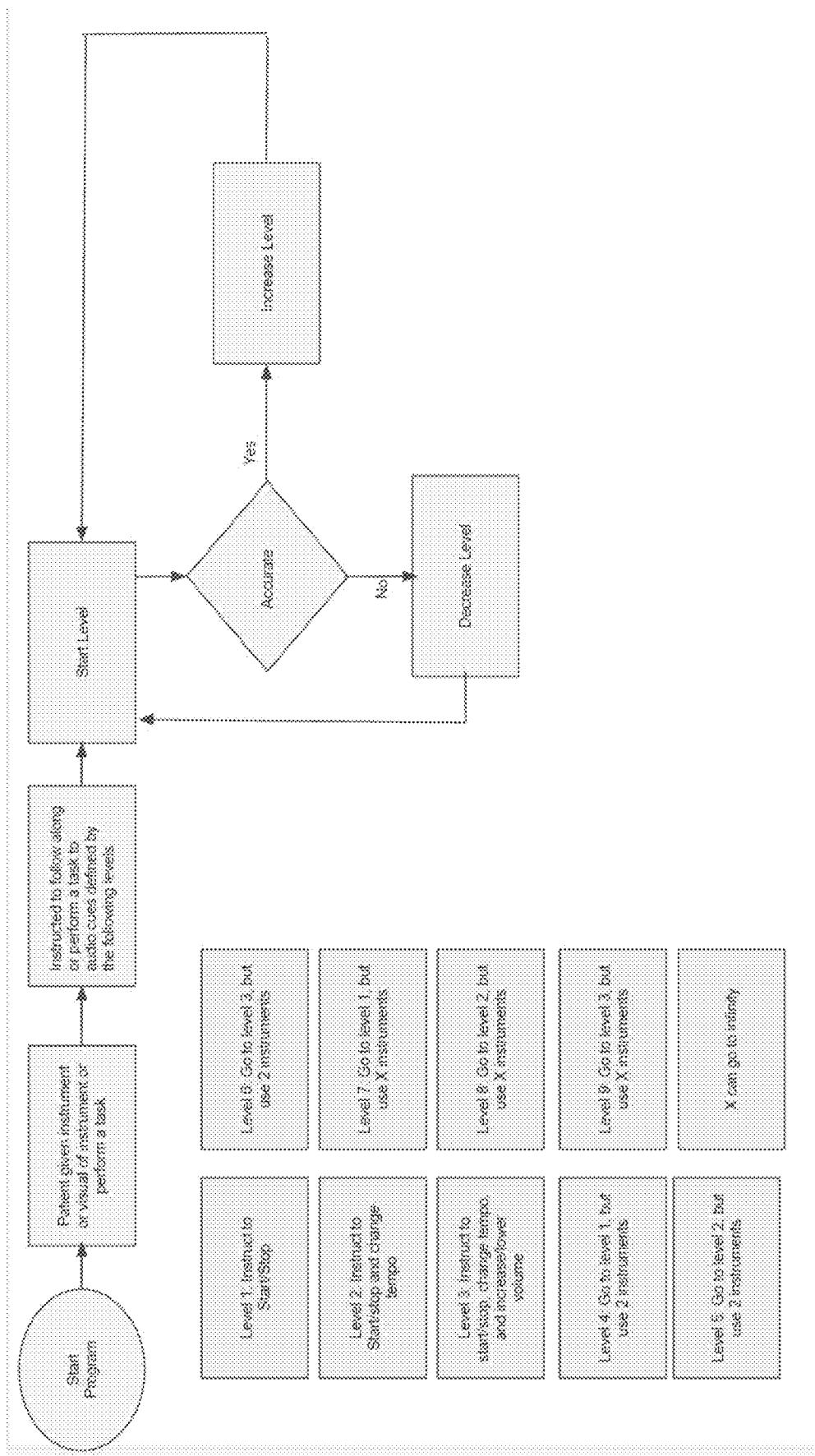
FIGS. 26-28 illustrates an implementation of a technique for attention training of a patient in accordance with exemplary embodiments of the disclosed subject matter.
Figure 27:
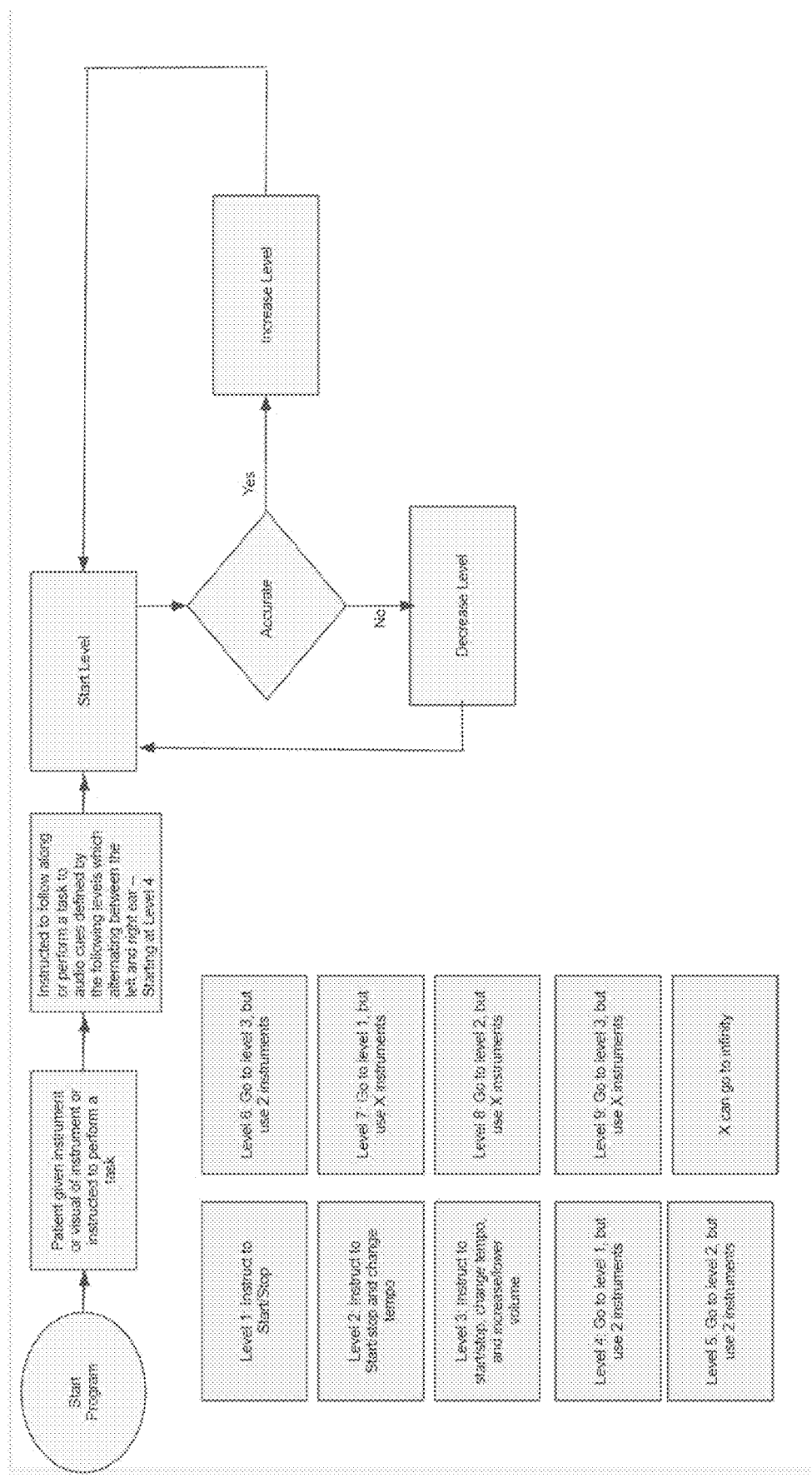
Figure 28:
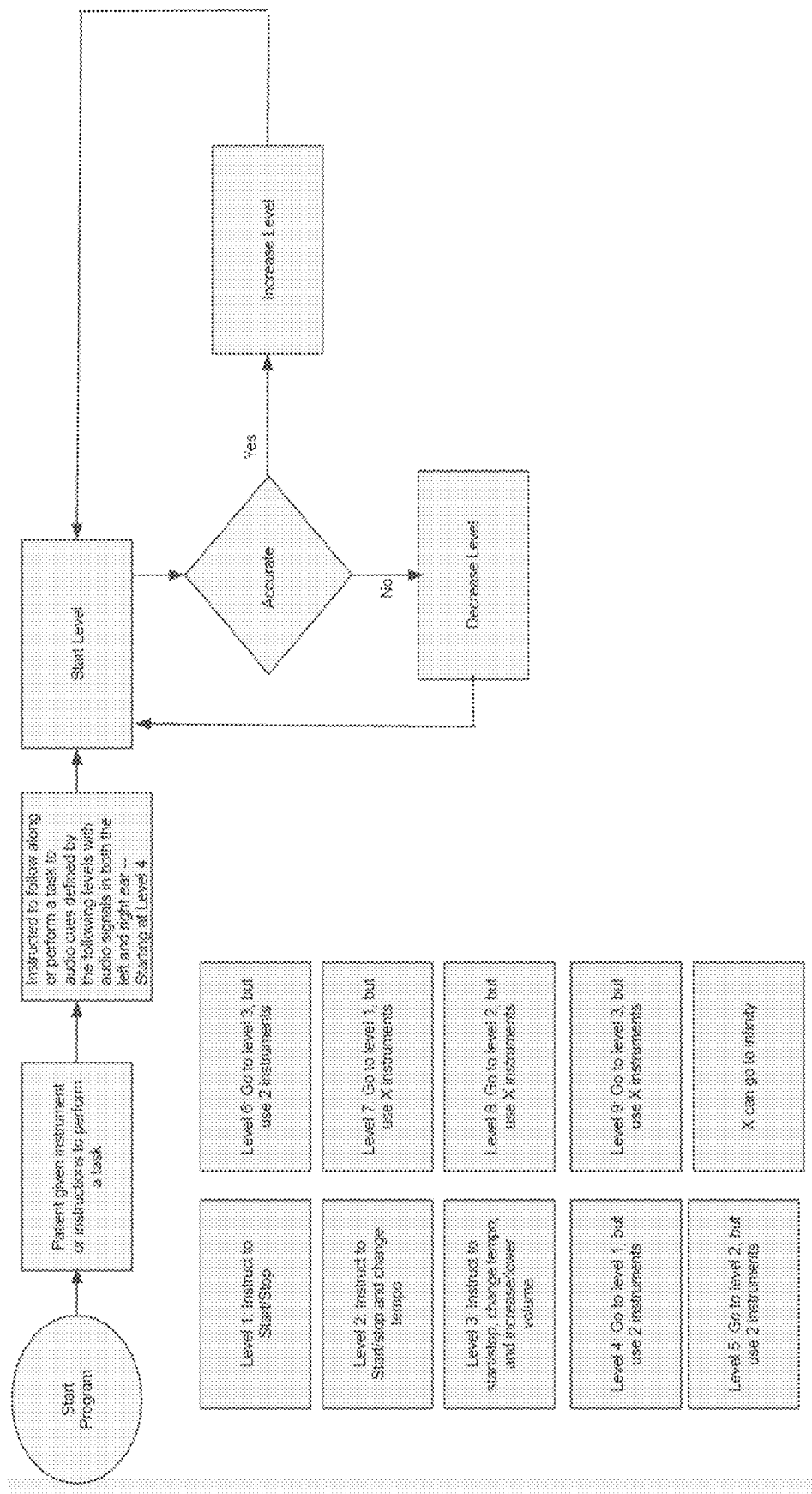

FIGS. 26-28 illustrate a technique useful for attention training. For attention training, the system and methods described herein operate in a closed loop fashion to help patients sustain, divide, alternate and select attention. No visual cue is allowed to signal which movements to make. The appropriate populations include patients with brain tumor, multiple sclerosis, Parkinson's disease, and neurological disease and injury.

The flow diagram illustrated in FIG. 26 for sustained attention training is substantially identical to the flow illustrated in FIG. 18 for gait training, with the differences noted herein. As with gait training, the patient is provided with an instrument (e.g., any instrument could work, such as a drumstick, drum, keyboard, or wirelessly connected version of each) and is instructed, either by cues appearing on the display 222 or verbally by a therapist, to follow along or perform a task to audio cues defined by levels 1 through 9 as illustrated in FIG. 26. The analytics system 108 evaluates the patient's ability to accurately complete the task and classifies the responses to change the tempo or the difficulty of the task. Similarly, FIG. 27 illustrates a flow diagram for alternating attention training in which the instructions are provided, either by cues appearing on the display 222 or verbally by a therapist, to follow along or perform a task to audio cues which alternate between the left and the right ear. FIG. 28 illustrates a flow diagram for divided attention in which the instructions are provided to follow along or perform a task to audio cues with audio signals in both the left and right ear.

Figure 29:
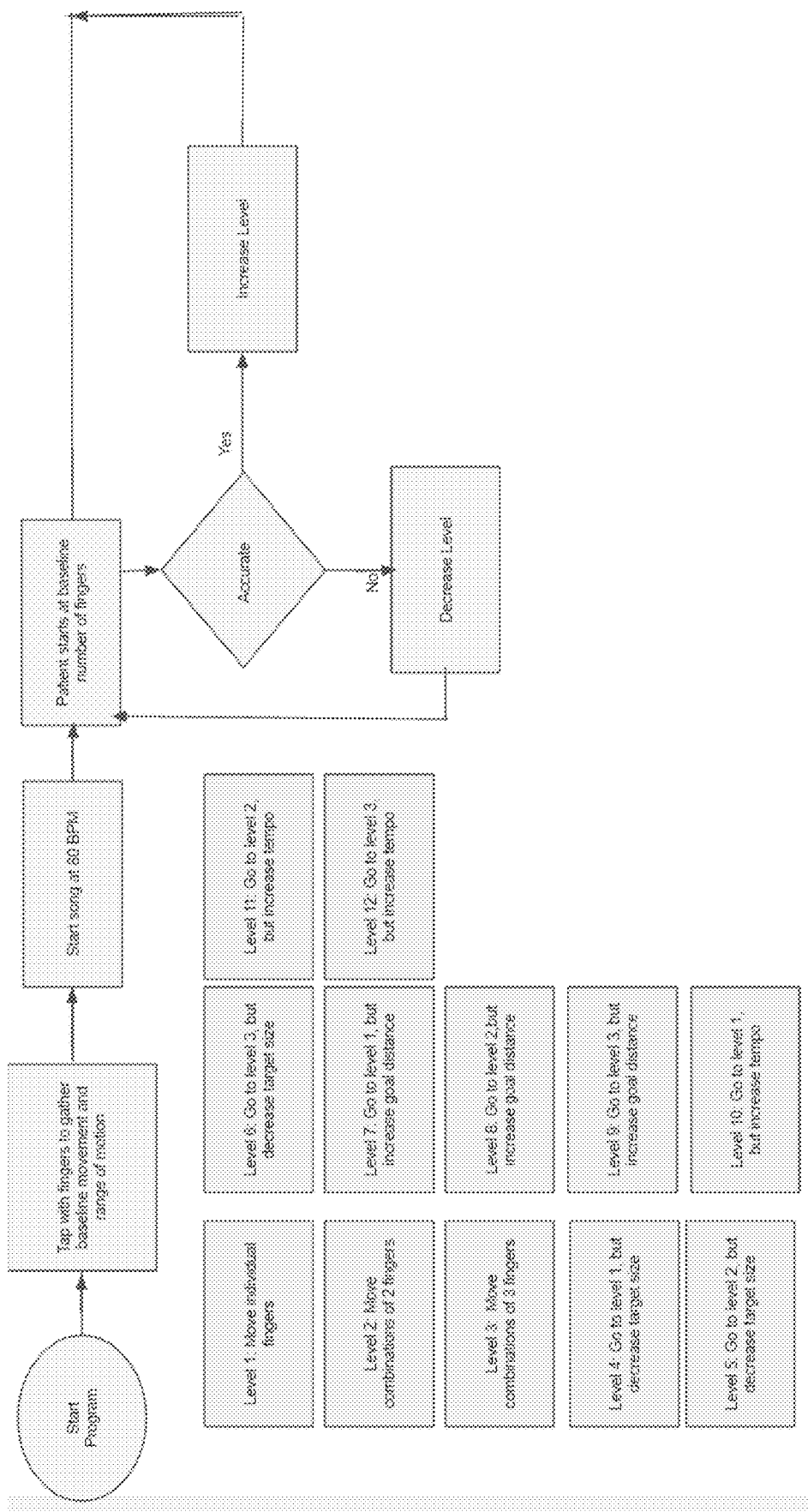
FIG. 29 illustrates an implementation of a technique for dexterity training of a patient in accordance with exemplary embodiments of the disclosed subject matter.

The flow diagram illustrated in FIG. 29 for dexterity training is substantially identical to the flow illustrated in FIG. 18 for gait training, with the differences noted herein. For dexterity training, the patient is instructed to tap with their fingers on the keyboard of the piano to gather baseline movement and range of motion information. The song is started at a particular beat per minute, and the patient starts tapping with the baseline number of fingers. The analytics system 108 evaluates the patient's ability to accurately complete the task and classifies the responses to change the tempo or the difficulty of the task.

Figure 30:
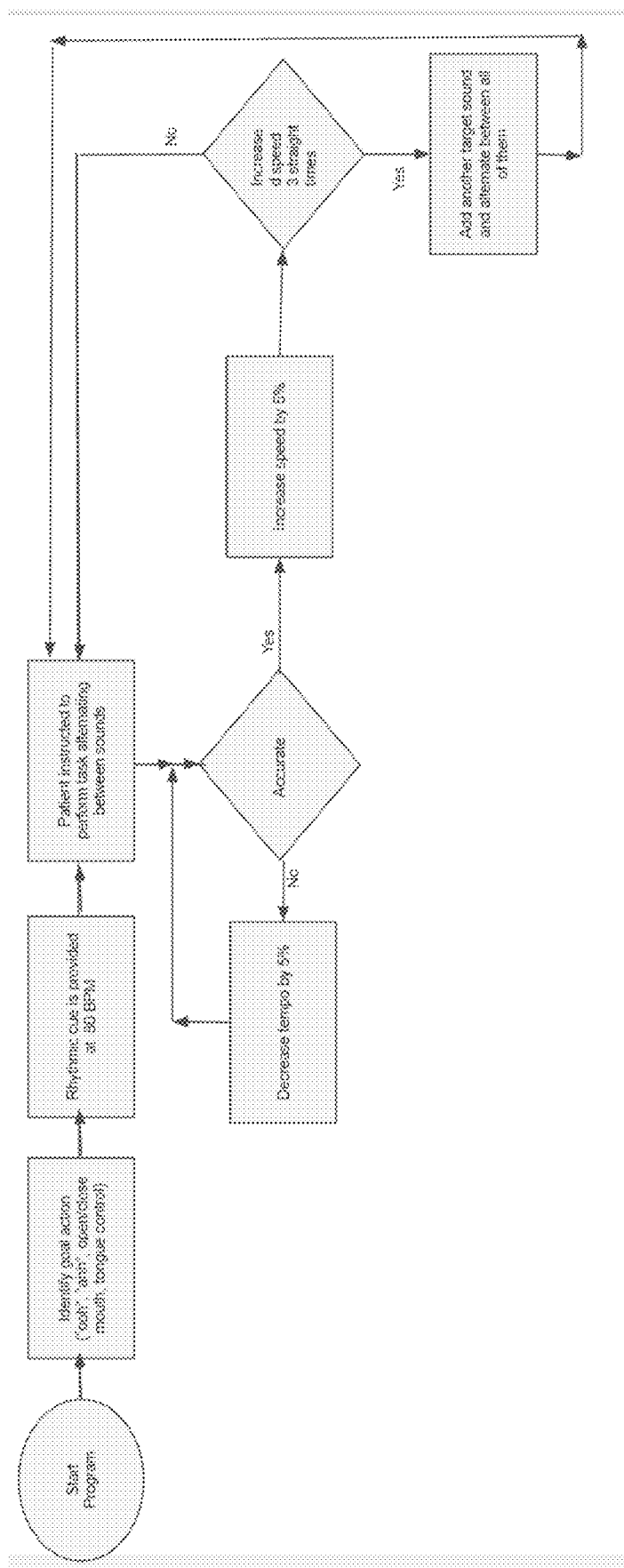
FIG. 30 illustrates an implementation of a technique for oral motor training of a patient in accordance with exemplary embodiments of the disclosed subject matter.

The flow diagram illustrated in FIG. 30 for oral motor training is substantially identical to the flow illustrated in FIG. 18 for gait training, with the differences noted herein. For oral motor training, the patient is instructed to perform a task alternating between two sounds, e.g., "ooh" and "aah." The analytics system 108 evaluates the patient's ability to accurately complete the task and classifies the responses to change the tempo or the difficulty of the task, e.g., by providing a different target sound.

Figure 31:
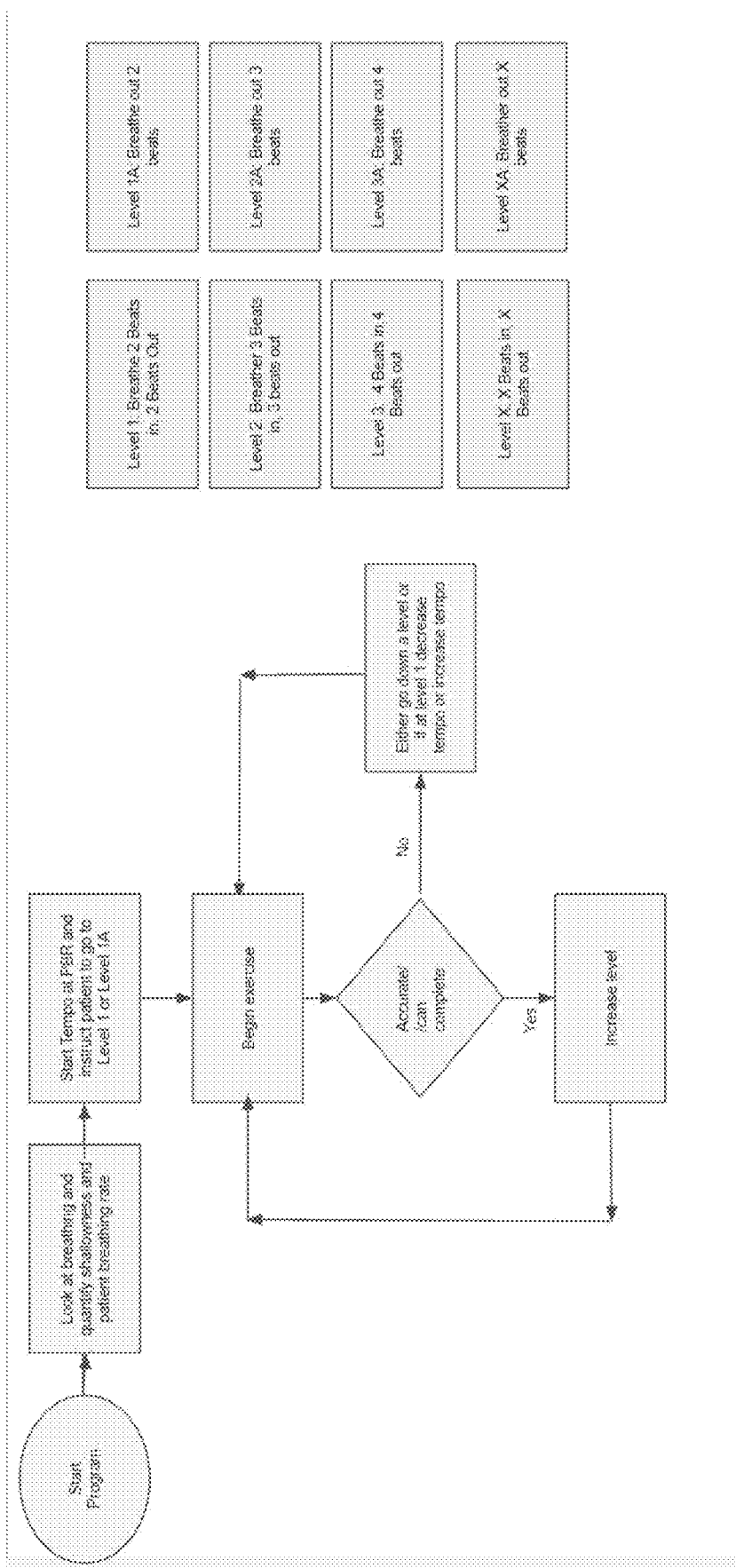
FIG. 31 illustrates an implementation of a technique for respiratory training of a patient in accordance with exemplary embodiments of the disclosed subject matter.

The flow diagram illustrated in FIG. 31 for respiratory training is substantially identical to the flow illustrated in FIG. 18 for gait training, with the differences noted herein. For respiratory training, a baseline breathing rate and shallowness of breathing is determined. Music is provided with a baseline tempo at the patient's breathing rate, and the patient is instructed to perform breathing tasks has described in the levels in FIG. 31. The analytics system 108 evaluates the patient's ability to accurately complete the task and classifies the responses to change the tempo or the difficulty of the task, e.g., by providing a different breathing pattern.

The above systems, devices, methods, processes, and the like may be realized in hardware, software, or any combination of these suitable for an application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in several ways. At the same time, processing may be distributed across devices such as the various systems described above, or all the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless an order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure.

What is claimed is:

1. A method for rehabilitation of a patient having a physical impairment by providing music therapy during a therapy session in which the patient is provided music having beat signals at a beat tempo, the beat signals each being output at a respective output time, and in which the patient attempts to perform repetitive movements in time with the beat signals, the method being implemented on a computer system having one or more physical processors configured by machine-readable instructions which, when executed perform the method, comprising:

receiving time-stamped biomechanical data of the patient relating to the repetitive movements, wherein each repetitive movement is performed by the patient in time with an associated beat signal among the beat signals, and wherein the biomechanical data is measured using a sensor;

analyzing the time-stamped biomechanical data to identify an onset time of one or more of the repetitive movements;

measuring a delay between the onset time and the output time of the associated beat signal;

determining an entrainment parameter based on the measured delay;

modifying the music based on the entrainment parameter; and continuing the therapy session using the modified music.

2. The method of claim 1, further comprising:
measuring the biomechanical data from the patient, wherein measuring the biomechanical data from the patient comprises providing a sensor associated with the patient and measuring one or more of motion, acceleration and pressure associated with movement of the patient.

3. The method of claim 2, wherein measuring the biomechanical data from the patient comprises one or more of: capturing movement data using an inertial measurement units (IMU) device, and capturing video associated with movement of the patient using an image capture device.

4. The method of claim 1, wherein modifying the music includes: adjusting the beat tempo in relation to a goal beat tempo based on the entrainment parameter.

5. The method of claim 1, wherein modifying the music includes at least one of: adjusting the beat tempo in relation to a goal beat tempo, modifying one or more of the beat signals, adjusting a chord of the music, adjusting a volume of the music, adjusting a meter of the music, adding one or more audible cues to the music, adding a rhythmic component to the music, adjusting a tempo of the music.

6. The method of claim 1, further comprising: providing a cue to the patient to perform each repetitive movement in time with an associated beat signal, wherein providing a cue to the patient to perform each repetitive movement comprises providing a visual or audible or haptic cue to the patient in relation to the associated beat signal.

7. The method of claim 1, further comprising:
comparing the beat tempo to a goal beat tempo; and
wherein the music is modified as a function of the beat tempo comparison and the calculated entrainment potential.

8. The method of claim 1, wherein determining an entrainment parameter comprises determining a delay between the respective onset time of each of a plurality of repetitive movements and the respective output-time of the associated beat signals in real-time, and wherein the identified onset time for a given repetitive movement is a time at which a prescribed identifiable event occurs during the given repetitive movement.

9. The method of claim 1, further comprising, if the delay between the beat signal and the onset time of the repetitive movements individually measured for each of the plurality of repetitive movements occurring over a period of time is substantially constant, increasing the beat tempo towards a goal beat tempo.

10. The method of claim 1, further comprising: providing music to the patient by one or more of: selecting music having beat signals at the beat tempo, and modifying existing music to have beat signals at the beat tempo.

11. The method of claim 1, wherein the repetitive movement comprises the patient's gait, the method further comprising:
analyzing the biomechanical data to classify a symmetry of the patient's gait;
modifying the music as a function of the entrainment parameter and classification of the symmetry of the patient's gait.

12. The method of claim 1, further comprising:
analyzing the biomechanical data to classify a deficit in the repetitive movement;
modifying the music as a function of the entrainment parameter and based on the classification of the deficit.

13. The method of claim 1, further comprising:
receiving an initial set of biomechanical data from the patient regarding the repetitive movements of the patient,
determining, based on the initial set of biomechanical data, a baseline condition for the patient; and
determining the beat tempo based on the baseline condition.

14. A system for rehabilitation of a patient having a physical impairment by providing music therapy during a therapy session in which the patient is provided music having beat signals at a beat tempo, the beat signals each being output at a respective output time, and in which the patient performs repetitive movements in time with the beat signals, the system comprising
a computer system having one or more physical processors configured by machine-readable instructions to:
receive time-stamped biomechanical data of the patient and time-stamped beat signals, wherein time-stamped biomechanical data relates to each repetitive movement performed by the patient in relation to one of the beat signals, wherein the biomechanical data is measured using a sensor associated with the patient, and wherein the received time-stamped beat signals represent the respective output time of the beat signals;
analyze the time-stamped biomechanical data to identify an onset time of one of more of the repetitive movements;
determine, for each of the one or more repetitive movements, a delay between the identified onset time and the respective output time of the beat signal;
calculate an entrainment parameter based on the measured delay;
provide instructions to modify the music based on the entrainment parameter, wherein the therapy session is continued using the modified music.

15. The system of claim 14, further comprising:
a music delivery device for providing the music to the patient; and
the sensor associated with the patient and measuring the time-stamped biomechanical data.

16. The system of claim 15, wherein the instructions to modify the music include instructions to at least one of: adjust the beat tempo in relation to a goal beat tempo, modify one or more of the beat signals, adjust a chord of the music, adjust a volume of the music, adjust a meter of the music, add one or more audible cues to the music, add a rhythmic component to the music, and adjust a tempo of the music.

17. The system of claim 14, wherein the instructions to modify the music are provided as a function of a difference between the beat tempo and a goal beat tempo and the determined entrainment potential.

18. The system of claim 14, wherein the computer system is configured to determine the entrainment parameter by determining the delay between the respective onset time of each of a plurality of repetitive movements and the respective output-time of the associated beat signals in real-time, and wherein the identified onset time for a given repetitive movement is a time at which a prescribed identifiable event occurs during the given repetitive movement.

19. The system of claim 14,
wherein the computer system is configured by machine-readable instructions to
analyze the biomechanical data to classify a deficit in the repetitive movement; and if the patient's initiation is problematic, provide instructions to modify the music as a function of the entrainment parameter and based on the classification of the deficit.

20. A method for rehabilitation of a patient having a physical impairment by providing rhythmic audio therapy, the method being implemented during a therapy session in which a patient is provided rhythmic audio content having beat signals at a beat tempo, the beat signals each being output at a respective output time, and in which the patient attempts to repeatedly perform a repetitive movement in time with the beat signals, the method being implemented on a computer system having a processor configured by machine-readable instructions which, when executed perform the method, comprising:
  receiving time-stamped biomechanical data of the patient relating to the repetitive movements performed by the patient, wherein each repetitive movement is performed in relation to an associated beat signal among the beat signals, and wherein the biomechanical data is measured using a sensor;
  determining, based on the time-stamped biomedical data and the output times of the associated beat signals, a temporal relationship between each repetitive movement and its associated beat signal, respectively;
  calculating an entrainment parameter based on the temporal relationship respectively determined for one or more of the repetitive movements; and
  modifying the rhythmic audio content being output to the patient based on the determined entrainment parameter; and
  continuing the therapy session using the modified music.

21. The method of claim 20, wherein the receiving, determining, calculating and modifying steps are repeated throughout the therapy session whereby the rhythmic audio content output to the patient is dynamically modified in near real-time as a function of the entrainment parameter.

22. The method of claim 20, further comprising:
  providing the rhythmic audio content to the patient using an audio output device; and
  measuring the biomechanical data from the patient using the sensor associated with the patient.

23. The method of claim 20, wherein modifying the rhythmic audio content includes at least one of: adjusting the beat tempo in relation to a goal beat tempo, modifying one or more of the beat signals, adjusting a chord of the rhythmic audio content, adjusting a volume of the rhythmic audio content, adjusting a meter of the rhythmic audio content, adding one or more audible cues to the rhythmic audio content, adding a rhythmic component to the rhythmic audio content, adjusting a tempo of the music.

24. The method of claim 20, further comprising: providing a cue to the patient to perform each repetitive movement in time with an associated beat signal, wherein providing a cue to the patient to perform each repetitive movement comprises providing a visual or audible or haptic cue to the patient in relation to the associated beat signal.

25. The method of claim 20, further comprising:
  analyzing the biomechanical data to evaluate a deficit in the repetitive movement;
  modifying the rhythmic audio content as a function of the entrainment parameter and based on the evaluation of the deficit.

* * * * *